(12) United States Patent
Chirik et al.

(10) Patent No.: US 10,494,395 B2
(45) Date of Patent: Dec. 3, 2019

(54) BASE METAL CATALYZED BORYLATION OF ARENES AND AROMATIC HETEROCYCLES

(71) Applicant: THE TRUSTEES OF PRINCETON UNIVERSITY, Princeton, NJ (US)

(72) Inventors: Paul J. Chirik, Princeton, NJ (US); Scott Semproni, Portland, OR (US); Jennifer Obligacion, Edison, NJ (US); Margaret Scheuermann, Plainsboro, NJ (US)

(73) Assignee: The Trustees of Princeton University, Princeton, NJ (US)

( * ) Notice: Subject to any disclaimer, the term of this patent is extended or adjusted under 35 U.S.C. 154(b) by 0 days.

(21) Appl. No.: 15/103,200

(22) PCT Filed: Dec. 9, 2014

(86) PCT No.: PCT/US2014/069412
§ 371 (c)(1),
(2) Date: Jun. 9, 2016

(87) PCT Pub. No.: WO2015/089119
PCT Pub. Date: Jun. 18, 2015

(65) Prior Publication Data
US 2016/0318963 A1 Nov. 3, 2016

Related U.S. Application Data

(60) Provisional application No. 61/913,522, filed on Dec. 9, 2013.

(51) Int. Cl.
*C07F 15/06* (2006.01)
(52) U.S. Cl.
CPC .................. *C07F 15/065* (2013.01)

(58) Field of Classification Search
CPC ..... C07F 15/065; C07F 15/06; C07F 15/0053
See application file for complete search history.

(56) References Cited

U.S. PATENT DOCUMENTS

2001/0039349 A1  11/2001  Hartwig et al.

FOREIGN PATENT DOCUMENTS

| WO | 2012025760 A1 | 3/2012 |
| WO | 2013043783 A2 | 3/2013 |

OTHER PUBLICATIONS

Gurdev (Indian Journal of Chemistry, Section A:Inorganic, physical, Theoritical and Analytical; 1990, 29A(12, 1222-4). Abstract.*
International Search Report and Written Opinion issued in corresponding International Application No. PCT/US2014/069412 dated Feb. 25, 2015, 10 pages.
Obligacion, Jennifer V. et al., Highly Selective Bis(imino)pyridine Iron-Catalyzed Alkene Hydroboration, Organic Letters, 2013, vol. 15, No. 11, pp. 2680-2683, published on web May 21, 2013.
Lin, Tzu-Pin et al., Boryl-Mediated Reversible H2 Activation at Cobalt: Catalytic Hydrogenation, Dehydrogenation and Transfer Hydrogen, Journal of the American Chemical Society, 2013, vol. 135, pp. 15310-15313.
Nishimura, Takahiro et al., Cobalt-Catalyzed Conjugate Addition of Silylacetylenes to a B-Unsaturated Ketones, Chemical Communications, 2011, vol. 47, pp. 10142-10144.
Fessenden et al., Organic Chemistry, 5th Ed. Brooks/Cole Publishing Co., 1993 pp. 482-499.

* cited by examiner

*Primary Examiner* — Pancham Bakshi
(74) *Attorney, Agent, or Firm* — J. Clinton Wimbish; Nexsen Pruet, PLLC

(57) ABSTRACT

In one aspect, cobalt complexes are described herein. In some embodiments, such cobalt complexes employ bis(phosphine) or bis(imine) ligand and are operable as catalysts for borylation of arenes and aromatic heterocycles.

9 Claims, 4 Drawing Sheets

BASE METAL CATALYZED BORYLATION OF ARENES AND AROMATIC HETEROCYCLES

RELATED APPLICATION DATA

This application is a U.S. National Phase of PCT/US2014/069412, filed Dec. 9, 2014, which claims priority pursuant to 35 U.S.C. § 119(e) to U.S. Provisional Patent Application Ser. No. 61/913,522 filed Dec. 9, 2013, each of which is incorporated herein by reference in their entireties.

STATEMENT OF GOVERNMENT RIGHTS

This invention was made with government support under Grant Nos. CHE1026084 and CHE1265988 awarded by the National Science Foundation. The government has certain rights in the invention.

FIELD

The present invention relates to cobalt complexes and, in particular, to use of cobalt complexes as catalysts in borylation of aromatic compounds.

BACKGROUND

Carbon-hydrogen bonds are abundant in most organic molecules, and methods for their direct, selective catalytic functionalization are attractive as an efficient means to access more complex molecular entities. The transition-metal-catalyzed borylation of heterocycles and arenes has emerged as one of the most effective and efficient methods for C—H functionalization, in part due to the versatility of the resulting aryl boronate esters in synthesis. Catalytic borylation activity has been observed with several transition-metal complexes, although in most cases the synthetic utility is limited by poor activity or photochemical methods required for catalyst activation. Iridium diene complexes such as [Ir(COD)OMe]$_2$ (COD=1,5-cyclooctadiene) in combination with substituted bipyridine or phenanthroline ligands are the most widely used catalysts for C—H borylation. Silica-supported monophosphine rhodium and iridium catalysts as well as iridium nanoparticles in ionic liquids have also been reported and offer reactivity and selectivity advantages over their soluble counterparts. Despite their widespread application, the number of precious metal catalysts reported in the literature that enable efficient turnover is limited. Therefore, the development of new, readily accessible and modular catalyst platforms is required for expanding the scope and utility of metal-catalyzed C—H borylation.

SUMMARY

In one aspect, cobalt complexes are described herein. In some embodiments, such cobalt complexes employ bis(phosphine) or bis(imine) ligand and are operable as catalysts for borylation of arenes and aromatic heterocycles. A cobalt complex described herein, in some embodiments, is of Formula (I):

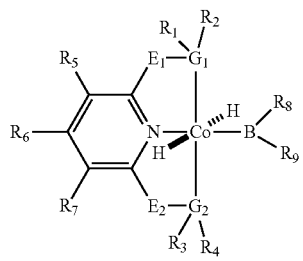

(I)

wherein $R_1$-$R_7$ are independently selected from the group consisting of hydrogen, alkyl, heteroalkyl, cycloalkyl, heterocycloalkyl, aryl, heteroaryl, alkyl-aryl and alkyl-heteroaryl, wherein the alkyl, heteroalkyl, cycloalkyl, heterocycloalkyl, aryl, heteroaryl, alkyl-aryl and alkyl-heteroaryl are optionally substituted with one or more substituents selected from the group consisting of ($C_1$-$C_{10}$)-alkyl, ($C_1$-$C_{10}$)-alkenyl, alkoxy, halo, hydroxy, C(O)O$R_{10}$, N$R_{11}$$R_{12}$, wherein $R_{10}$-$R_{12}$ are independently selected from the group consisting of hydrogen, ($C_1$-$C_{10}$)-alkyl and ($C_1$-$C_{10}$)-alkenyl; and wherein $R_8$ and $R_9$ are independently selected from the group consisting of hydrogen, alkyl and alkoxy, wherein $R_8$ and $R_9$ may optionally form a substituted or unsubstituted cyclic structure or ring; and wherein $E_1$ and $E_2$ are independently selected from the group consisting of $CR_{13}$, $C(R_{13})_2$, O, S and $NR_{14}$, wherein $R_{13}$ and $R_{14}$ are independently selected from the group consisting of hydrogen, alkyl, heteroalkyl, aryl and heteroaryl; and wherein $G_1$ and $G_2$ are independently selected from N and P; and wherein any two of $R_1$-$R_7$ that are vicinal to one another may optionally form a substituted or unsubstituted, saturated or unsaturated, cyclic structure or ring.

In another aspect, a cobalt complex is of Formula (II):

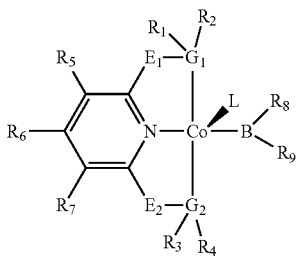

(II)

wherein $R_1$-$R_7$ are independently selected from the group consisting of hydrogen, alkyl, heteroalkyl, cycloalkyl, heterocycloalkyl, aryl, heteroaryl, alkyl-aryl and alkyl-heteroaryl, wherein the alkyl, heteroalkyl, cycloalkyl, heterocycloalkyl, aryl, heteroaryl, alkyl-aryl and alkyl-heteroaryl are optionally substituted with one or more substituents selected from the group consisting of ($C_1$-$C_{10}$)-alkyl, ($C_1$-$C_{10}$)-alkenyl, alkoxy, halo, hydroxy, C(O)O$R_{10}$, N$R_{11}$$R_{12}$, wherein $R_{10}$-$R_{12}$ are independently selected from the group consisting of hydrogen, ($C_1$-$C_{10}$)-alkyl and ($C_1$-$C_{10}$)-alkenyl; and wherein $R_8$ and $R_9$ are independently selected from the group consisting of hydrogen, alkyl and alkoxy, wherein $R_8$ and $R_9$ may optionally form a substituted or unsubstituted cyclic structure or ring; and wherein $E_1$ and $E_2$ are independently selected from the group consisting of $CR_{13}$, $C(R_{13})_2$, O, S and $NR_{14}$, wherein $R_{13}$ and $R_{14}$ are independently selected from the group consisting of hydrogen, alkyl, heteroalkyl, aryl and heteroaryl; and wherein $G_1$ and $G_2$ are independently selected from N and P; and wherein L is selected from the group consisting of $N_2$, CO, phosphine, tetrahydrofuran, amine, alkoxy and inert to electron donor ligand; and wherein any two of $R_1$-$R_7$ that are vicinal to one another may optionally form a substituted or unsubstituted, saturated or unsaturated, cyclic structure or ring.

In another aspect a cobalt complex is of Formula (III):

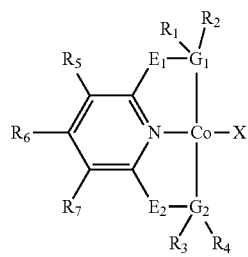

(III)

wherein $R_1$-$R_7$ are independently selected from the group consisting of hydrogen, alkyl, heteroalkyl, cycloalkyl, heterocycloalkyl, aryl, heteroaryl, alkyl-aryl and alkyl-heteroaryl, wherein the alkyl, heteroalkyl, cycloalkyl, heterocycloalkyl, aryl, heteroaryl, alkyl-aryl and alkyl-heteroaryl are optionally substituted with one or more substituents selected from the group consisting of ($C_1$-$C_{10}$)-alkyl, ($C_1$-$C_{10}$)-alkenyl, alkoxy, halo, hydroxy, $C(O)OR_{10}$, $NR_{11}R_{12}$, wherein $R_{10}$-$R_{12}$ are independently selected from the group consisting of hydrogen, ($C_1$-$C_{10}$)-alkyl and ($C_1$-$C_{10}$)-alkenyl; and wherein $E_1$ and $E_2$ are independently selected from the group consisting of $CR_8$, $C(R_8)_2$, O, S and $NR_9$, wherein $R_8$ and $R_9$ are independently selected from the group consisting of hydrogen, alkyl, heteroalkyl, aryl and heteroaryl; and wherein $G_1$ and $G_2$ are independently selected from N and P such that $G_1$ and $G_2$ are not both P; and wherein any two of $R_1$-$R_7$ that are vicinal to one another may optionally form a substituted or unsubstituted, saturated or unsaturated, cyclic structure or ring; and wherein X is selected from the group consisting of alkyl, heteroalkyl, aryl, heteroaryl, alkyl-aryl, alkyl-heteroaryl, aryl-alkyl, heteroaryl-alkyl, hydroxyl, alkoxy, halo, $R_{13}COO$— and —$B(R_{14})(R_{15})$, wherein $R^{13}$ is selected from the group consisting of alkyl, heteroalkyl, alkenyl, aryl and heteroaryl and $R_{14}$ and $R_{15}$ are independently selected from the group consisting of hydrogen, alkyl and alkoxy, wherein $R_{14}$ and $R_{15}$ may optionally form a substituted or unsubstituted cyclic structure or ring. In some embodiments, X is halo or BPin or $R_{13}COO$—, wherein $R_{13}$ is alkyl.

Alternatively, X is heteroalkyl of formula

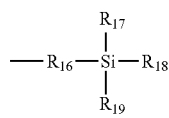

wherein $R_{16}$ is selected from the group consisting of alkyl, alkenyl, aryl, heteroaryl, alkyl-aryl, alkyl-heteroaryl, aryl-alkyl and heteroaryl-alkyl and $R_{17}$-$R_{19}$ are independently selected from the group consisting of hydrogen, alkyl, alkenyl, aryl, heteroaryl, alkyl-aryl, alkyl-heteroaryl, alkoxy and hydroxy. For example, in some embodiments, X is —$CH_2$—$Si(CH_3)_3$.

In another aspect, a cobalt complex is of Formula (IV):

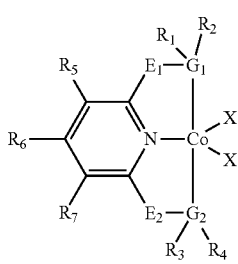

(IV)

wherein $R_1$-$R_7$ are independently selected from the group consisting of hydrogen, alkyl, heteroalkyl, cycloalkyl, heterocycloalkyl, aryl, heteroaryl, alkyl-aryl and alkyl-heteroaryl, wherein the alkyl, heteroalkyl, cycloalkyl, heterocycloalkyl, aryl, heteroaryl, alkyl-aryl and alkyl-heteroaryl are optionally substituted with one or more substituents selected from the group consisting of ($C_1$-$C_{10}$)-alkyl, ($C_1$-$C_{10}$)-alkenyl, alkoxy, halo, hydroxy, $C(O)OR_{10}$, $NR_{11}R_{12}$, wherein $R_{10}$-$R_{12}$ are independently selected from the group consisting of hydrogen, ($C_1$-$C_{10}$)-alkyl and ($C_1$-$C_{10}$)-alkenyl; and wherein $E_1$ and $E_2$ are independently selected from the group consisting of $CR_8$, $C(R_8)_2$, O, S and $NR_9$, wherein $R_8$ and $R_9$ are independently selected from the group consisting of hydrogen, alkyl, heteroalkyl, aryl and heteroaryl; and wherein $G_1$ and $G_2$ are independently selected from N and P; and wherein any two of $R_1$-$R_7$ that are vicinal to one another may optionally form a substituted or unsubstituted, saturated or unsaturated, cyclic structure or ring; and and wherein X is $R^{13}COO$—, where $R^{13}$ is selected from the group consisting of alkyl, heteroalkyl, alkenyl, aryl and heteroaryl. In some embodiments, wherein $G_1$ and $G_2$ are not each selected to be P, X is selected from the group consisting of halo and $R^{13}COO$—, where $R^{13}$ is selected from the group consisting of alkyl, heteroalkyl, alkenyl, aryl and heteroaryl.

In another aspect, a cobalt complex is of Formula (V):

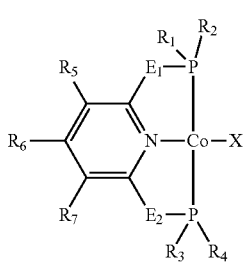

(V)

wherein $R_1$-$R_7$ are independently selected from the group consisting of hydrogen, alkyl, heteroalkyl, cycloalkyl, heterocycloalkyl, aryl, heteroaryl, alkyl-aryl and alkyl-heteroaryl, wherein the alkyl, heteroalkyl, cycloalkyl, heterocycloalkyl, aryl, heteroaryl, alkyl-aryl and alkyl-heteroaryl are optionally substituted with one or more substituents selected from the group consisting of $(C_1$-$C_{10})$-alkyl, $(C_1$-$C_{10})$-alkenyl, alkoxy, halo, hydroxy, $C(O)OR_{10}$, $NR_{11}R_{12}$, wherein $R_{10}$-$R_{12}$ are independently selected from the group consisting of hydrogen, $(C_1$-$C_{10})$-alkyl and $(C_1$-$C_{10})$-alkenyl; and wherein $E_1$ and $E_2$ are independently selected from the group consisting of $CR_8$, $C(R_8)_2$, O, S and $NR_9$, wherein $R_8$ and $R_9$ are independently selected from the group consisting of hydrogen, alkyl, heteroalkyl, aryl and heteroaryl; and wherein any two of $R_1$-$R_7$ that are vicinal to one another may optionally form a substituted or unsubstituted, saturated or unsaturated, cyclic structure or ring; and wherein X is selected from the group consisting of heteroalkyl, aryl, heteroaryl, alkyl-aryl, alkyl-heteroaryl, arylalkyl, heteroaryl-alkyl, hydroxyl, alkoxy, halo, $R_{13}COO$— and —$B(R_{14})(R_{15})$, wherein $R^{13}$ is selected from the group consisting of alkyl, heteroalkyl, alkenyl, aryl and heteroaryl and $R_{14}$ and $R_{15}$ are independently selected from the group consisting of hydrogen, alkyl and alkoxy, wherein $R_{14}$ and $R_{15}$ may optionally form a substituted or unsubstituted cyclic structure or ring. In some embodiments, X is chloro or BPin or $R_{13}COO$—, wherein $R_{13}$ is alkyl. Alternatively, X is heteroalkyl of formula

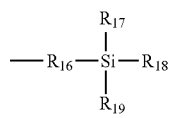

wherein $R_{16}$ is selected from the group consisting of alkyl, alkenyl, aryl, heteroaryl, alkyl-aryl, alkyl-heteroaryl, arylalkyl and heteroaryl-alkyl and $R_{17}$-$R_{19}$ are independently selected from the group consisting of hydrogen, alkyl, alkenyl, aryl, heteroaryl, alkyl-aryl, alkyl-heteroaryl, alkoxy and hydroxy. For example, in some embodiments, X is —$CH_2$—$Si(CH_3)_3$.

In a further aspect, a cobalt complex described herein is of Formula (VI):

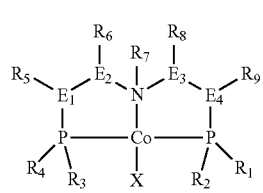

wherein $R_1$-$R_9$ are independently selected from the group consisting of hydrogen, alkyl, heteroalkyl, cycloalkyl, heterocycloalkyl, aryl, heteroaryl, alkyl-aryl and alkyl-heteroaryl, wherein the alkyl, heteroalkyl, cycloalkyl, heterocycloalkyl, aryl, heteroaryl, alkyl-aryl and alkyl-heteroaryl are optionally substituted with one or more substituents selected from the group consisting of $(C_1$-$C_{10})$-alkyl, $(C_1$-$C_{10})$-alkenyl, alkoxy, halo, hydroxy, $C(O)OR_{13}$, $NR_{14}R_{15}$, wherein $R_{13}$-$R_{15}$ are independently selected from the group consisting of hydrogen, $(C_1$-$C_{10})$-alkyl and $(C_1$-$C_{10})$-alkenyl and wherein $R_5$-$R_9$ may form part of a cyclic or aromatic system; and wherein $E_1$-$E_4$ are independently selected from the group consisting or $C(R_{11})_2$, $C(R_{11})$ and $Si(R_{12})_2$, wherein $R_{11}$ and $R_{12}$ are independently selected from the group consisting of hydrogen, alkyl and aryl; and wherein X is selected from the group consisting of halo, alkyl, heteroalkyl, aryl, heteroaryl, alkyl-aryl, alkyl-heteroaryl, aryl-alkyl, heteroaryl-alkyl, hydroxy and alkoxy.

In another aspect, methods of providing borylated products are described herein. For example a method of providing a borylated product comprises providing a reaction mixture including an arene or aromatic heterocycle and a cobalt complex having a boron-containing ligand and reacting the arene or aromatic heterocycle with the boron containing ligand, wherein the cobalt complex is of Formula (I):

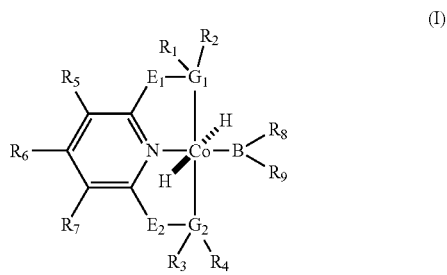

wherein $R_1$-$R_7$ are independently selected from the group consisting of hydrogen, alkyl, heteroalkyl, cycloalkyl, heterocycloalkyl, aryl, heteroaryl, alkyl-aryl and alkyl-heteroaryl, wherein the alkyl, heteroalkyl, cycloalkyl, heterocycloalkyl, aryl, heteroaryl, alkyl-aryl and alkyl-heteroaryl are optionally substituted with one or more substituents selected from the group consisting of $(C_1$-$C_{10})$-alkyl, $(C_1$-$C_{10})$-alkenyl, alkoxy, halo, hydroxy, $C(O)OR_{10}$, $NR_{11}R_{12}$, wherein $R_{10}$-$R_{12}$ are independently selected from the group consisting of hydrogen, $(C_1$-$C_{10})$-alkyl and $(C_1$-$C_{10})$-alkenyl; and wherein $R_8$ and $R_9$ are independently selected from the group consisting of hydrogen, alkyl and alkoxy, wherein $R_8$ and $R_9$ may optionally form a substituted or unsubstituted cyclic structure or ring; and wherein $E_1$ and $E_2$ are independently selected from the group consisting of $CR_{13}$, $C(R_{13})_2$, O, S and $NR_{14}$, wherein $R_{13}$ and $R_{14}$ are independently selected from the group consisting of hydrogen, alkyl, heteroalkyl, aryl and heteroaryl; and wherein $G_1$ and $G_2$ are independently selected from N and P; and wherein any two of $R_1$-$R_7$ that are vicinal to one another may optionally form a substituted or unsubstituted, saturated or unsaturated, cyclic structure or ring. In some embodiments, $R_8$ and $R_9$ are selected to form a cyclic boronate ester.

In another aspect, a method of providing a borylated product comprises providing a reaction mixture including an arene or aromatic heterocycle and a cobalt complex having a boron-containing ligand and reacting the arene or aromatic heterocycle with the boron containing ligand, wherein the cobalt complex is of Formula (II):

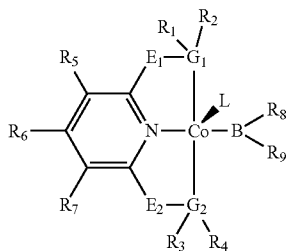

(II)

wherein $R_1$-$R_7$ are independently selected from the group consisting of hydrogen, alkyl, heteroalkyl, cycloalkyl, heterocycloalkyl, aryl, heteroaryl, alkyl-aryl and alkyl-heteroaryl, wherein the alkyl, heteroalkyl, cycloalkyl, heterocycloalkyl, aryl, heteroaryl, alkyl-aryl and alkyl-heteroaryl are optionally substituted with one or more substituents selected from the group consisting of $(C_1$-$C_{10})$-alkyl, $(C_1$-$C_{10})$-alkenyl, alkoxy, halo, hydroxy, $C(O)OR_{10}$, $NR_{11}R_{12}$, wherein $R_{10}$-$R_{12}$ are independently selected from the group consisting of hydrogen, $(C_1$-$C_{10})$-alkyl and $(C_1$-$C_{10})$-alkenyl; and wherein $R_8$ and $R_9$ are independently selected from the group consisting of hydrogen, alkyl and alkoxy, wherein $R_8$ and $R_9$ may optionally form a substituted or unsubstituted cyclic structure or ring; and wherein $E_1$ and $E_2$ are independently selected from the group consisting of $CR_{13}$, $C(R_{13})_2$, O, S and $NR_{14}$, wherein $R_{13}$ and $R_{14}$ are independently selected from the group consisting of hydrogen, alkyl, heteroalkyl, aryl and heteroaryl; and wherein $G_1$ and $G_2$ are independently selected from N and P; and wherein L is selected from the group consisting of $N_2$, CO, phosphine, tetrahydrofuran, amine, alkoxy and inert to electron donor ligand; and wherein any two of $R_1$-$R_7$ that are vicinal to one another may optionally form a substituted or unsubstituted, saturated or unsaturated, cyclic structure or ring. In some embodiments, $R_8$ and $R_9$ are selected to form a cyclic boronate ester.

In another aspect, a method of providing a borylated product comprises providing a reaction mixture including a cobalt complex, an arene or aromatic heterocycle and a borylation reagent and reacting the borylation reagent with the arene or aromatic heterocycle in the presence of the cobalt complex or a derivative thereof, the cobalt complex having Formula (III):

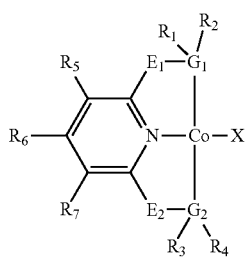

(III)

wherein $R_1$-$R_7$ are independently selected from the group consisting of hydrogen, alkyl, heteroalkyl, cycloalkyl, heterocycloalkyl, aryl, heteroaryl, alkyl-aryl and alkyl-heteroaryl, wherein the alkyl, heteroalkyl, cycloalkyl, heterocycloalkyl, aryl, heteroaryl, alkyl-aryl and alkyl-heteroaryl are optionally substituted with one or more substituents selected from the group consisting of $(C_1$-$C_{10})$-alkyl, $(C_1$-$C_{10})$-alkenyl, alkoxy, halo, hydroxy, $C(O)OR_{10}$, $NR_{11}R_{12}$, wherein $R_{10}$-$R_{12}$ are independently selected from the group consisting of hydrogen, $(C_1$-$C_{10})$-alkyl and $(C_1$-$C_{10})$-alkenyl; and wherein $E_1$ and $E_2$ are independently selected from the group consisting of $CR_8$, $C(R_8)_2$, O, S and $NR_9$, wherein $R_8$ and $R_9$ are independently selected from the group consisting of hydrogen, alkyl, heteroalkyl, aryl and heteroaryl; and wherein $G_1$ and $G_2$ are independently selected from N and P; and wherein any two of $R_1$-$R_7$ that are vicinal to one another may optionally form a substituted or unsubstituted, saturated or unsaturated, cyclic structure or ring; and wherein X is selected from the group consisting of alkyl, heteroalkyl, aryl, heteroaryl, alkyl-aryl, alkyl-heteroaryl, aryl-alkyl, heteroaryl-alkyl, hydroxyl, alkoxy, halo, $R_{13}COO$— and —$B(R_{14})(R_{15})$, wherein $R^{13}$ is selected from the group consisting of alkyl, heteroalkyl, alkenyl, aryl and heteroaryl and $R_{14}$ and $R_{15}$ are independently selected from the group consisting of hydrogen, alkyl and alkoxy, wherein $R_{14}$ and $R_{15}$ may optionally form a substituted or unsubstituted cyclic structure or ring.

In another aspect, a method of providing a borylated product comprises providing a reaction mixture including a cobalt complex, an arene or aromatic heterocycle and a borylation reagent and reacting the borylation reagent with the arene or aromatic heterocycle in the presence of the cobalt complex or a derivative thereof, the cobalt complex having Formula (IV):

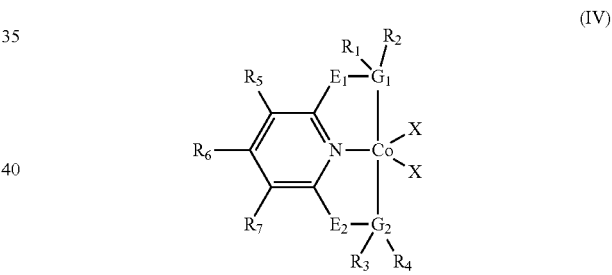

(IV)

wherein $R_1$-$R_7$ are independently selected from the group consisting of hydrogen, alkyl, heteroalkyl, cycloalkyl, heterocycloalkyl, aryl, heteroaryl, alkyl-aryl and alkyl-heteroaryl, wherein the alkyl, heteroalkyl, cycloalkyl, heterocycloalkyl, aryl, heteroaryl, alkyl-aryl and alkyl-heteroaryl are optionally substituted with one or more substituents selected from the group consisting of $(C_1$-$C_{10})$-alkyl, $(C_1$-$C_{10})$-alkenyl, alkoxy, halo, hydroxy, $C(O)OR_{10}$, $NR_{11}R_{12}$, wherein $R_{10}$-$R_{12}$ are independently selected from the group consisting of hydrogen, $(C_1$-$C_{10})$-alkyl and $(C_1$-$C_{10})$-alkenyl; and wherein $E_1$ and $E_2$ are independently selected from the group consisting of $CR_8$, $C(R_8)_2$, O, S and $NR_9$, wherein $R_8$ and $R_9$ are independently selected from the group consisting of hydrogen, alkyl, heteroalkyl, aryl and heteroaryl; and wherein $G_1$ and $G_2$ are independently selected from N and P; and wherein any two of $R_1$-$R_7$ that are vicinal to one another may optionally form a substituted or unsubstituted, saturated or unsaturated, cyclic structure or ring; and and wherein X is selected from the group consisting of halo and $R^{13}COO$—, where $R^{13}$ is selected from the group consisting of alkyl, heteroalkyl, alkenyl, aryl and heteroaryl. In some embodiments, wherein X is selected as halo, the reaction mixture further comprises an activator operable for activating the cobalt complex for catalysis. In such embodiments, the arene or aromatic heterocycle is reacted with the borylation reagent in the presence of the activated cobalt complex or a derivative of the activated cobalt complex.

In a further aspect, a method of providing a borylated product comprises providing a reaction mixture including a cobalt complex, an arene or aromatic heterocycle and a borylation reagent and reacting the borylation reagent with the arene or aromatic heterocycle in the presence of the cobalt complex or a derivative thereof, the cobalt complex having Formula (VI):

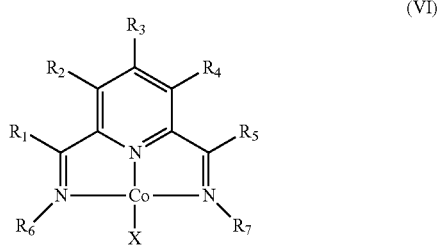

(VI)

wherein $R_1$-$R_7$ are independently selected from the group consisting of hydrogen, alkyl, heteroalkyl, cycloalkyl, heterocycloalkyl, aryl, heteroaryl, alkyl-aryl and alkyl-heteroaryl, wherein the alkyl, heteroalkyl, cycloalkyl, heterocycloalkyl, aryl, heteroaryl, alkyl-aryl and alkyl-heteroaryl are optionally substituted with one or more substituents selected from the group consisting of ($C_1$-$C_{10}$)-alkyl, ($C_1$-$C_{10}$)-alkenyl, alkoxy, halo, hydroxy, C(O)O$R_8$, N$R_9R_{10}$, wherein $R_8$-$R_{10}$ are independently selected from the group consisting of hydrogen, ($C_1$-$C_{10}$)-alkyl and ($C_1$-$C_{10}$)-alkenyl and wherein X is selected from the group consisting of alkyl, heteroalkyl, aryl, heteroaryl, alkyl-aryl, alkyl-heteroaryl, aryl-alkyl, heteroaryl-alkyl, halo, hydroxy and alkoxy.

These and other embodiments are described in further detail in the detailed description which follows.

DETAILED DESCRIPTION

Figure 1:
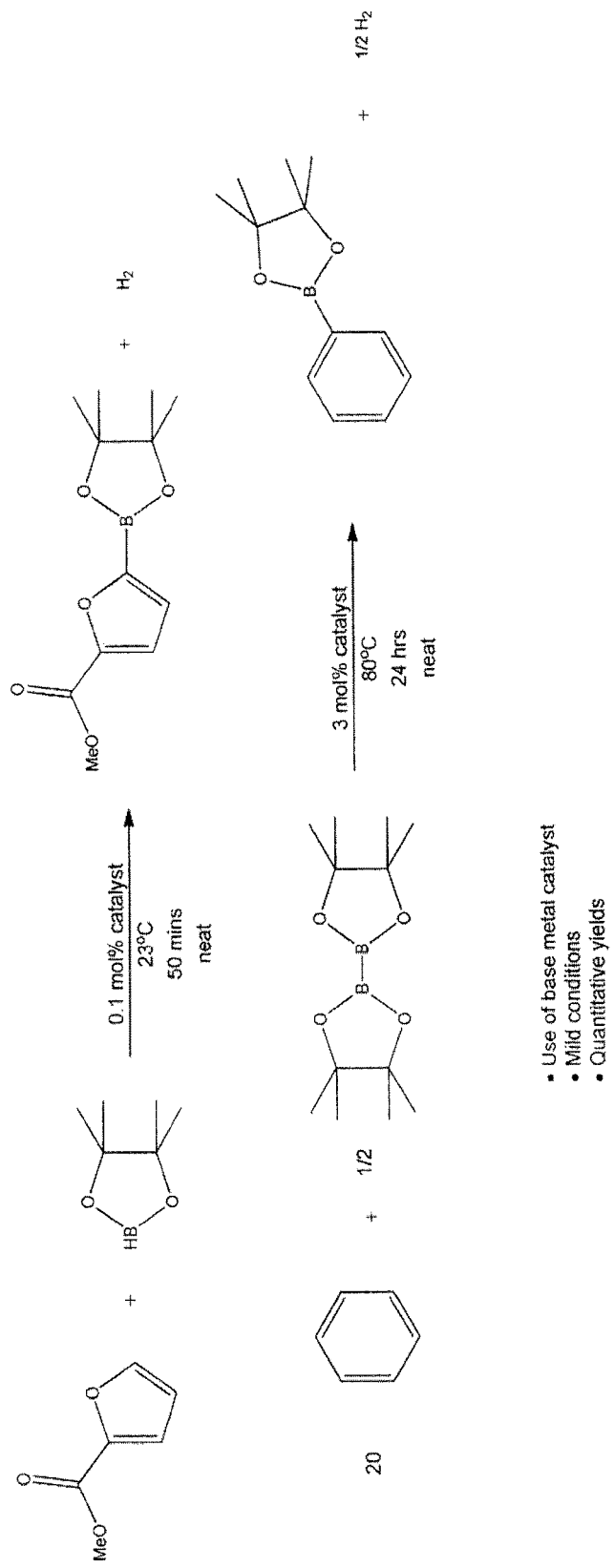
FIG. 1 illustrates borylation of an aromatic heterocycle and an arene in the presence of cobalt complex described herein according to some embodiments.

Embodiments described herein can be understood more readily by reference to the following detailed description and examples and their previous and following descriptions. Elements, apparatus and methods described herein, however, are not limited to the specific embodiments presented in the detailed description and examples. It should be recognized that these embodiments are merely illustrative of the principles of the present invention. Numerous modifications and adaptations will be readily apparent to those of skill in the art without departing from the spirit and scope of the invention.

Definitions

The term "alkyl" as used herein, alone or in combination, refers to a straight or branched saturated hydrocarbon group optionally substituted with one or more substituents. For example, an alkyl can be $C_1$-$C_{30}$ or $C_1$-$C_{18}$.

The term "alkenyl" as used herein, alone or in combination, refers to a straight or branched chain hydrocarbon group having at least one carbon-carbon double bond and optionally substituted with one or more substituents The term "aryl" as used herein, alone or in combination, refers to an aromatic monocyclic or multicyclic ring system optionally substituted with one or more ring substituents.

The term "heteroaryl" as used herein, alone or in combination, refers to an aromatic monocyclic or multicyclic ring system in which one or more of the ring atoms is an element other than carbon, such as nitrogen, boron, oxygen and/or sulfur.

The term "cycloalkyl" as used herein, alone or in combination, refers to a non-aromatic, mono- or multicyclic ring system optionally substituted with one or more ring substituents.

The term "heterocycloalkyl" as used herein, alone or in combination, refers to a non-aromatic, mono- or multicyclic ring system in which one or more of the atoms in the ring system is an element other than carbon, such as boron, nitrogen, oxygen, sulfur or phosphorus, alone or in combination, and wherein the ring system is optionally substituted with one or more ring substituents.

The term "heteroalkyl" as used herein, alone or in combination, refers to an alkyl moiety as defined above, having one or more carbon atoms in the chain, for example one, two or three carbon atoms, replaced with one or more heteroatoms, which may be the same or different. Heteroatoms, for example, include but are not limited to B, N, O, S and P.

The term "alkoxy" as used herein, alone or in combination, refers to the moiety RO—, where R is alkyl or alkenyl defined above.

The term "halo" as used herein, alone or in combination, refers to elements of Group VIIA of the Periodic Table (halogens). Depending on chemical environment, halo can be in a neutral or anionic state.

I. Cobalt Complexes

In one aspect, cobalt complexes are described herein. In some embodiments, such cobalt complexes employ bis (phosphine) or bis(imine) ligand and are operable as catalysts for borylation of arenes and aromatic heterocycles. A cobalt complex described herein, in some embodiments, is of Formula (I):

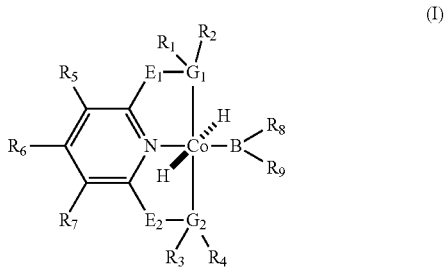

(I)

wherein $R_1$-$R_7$ are independently selected from the group consisting of hydrogen, alkyl, heteroalkyl, cycloalkyl, heterocycloalkyl, aryl, heteroaryl, alkyl-aryl and alkyl-heteroaryl, wherein the alkyl, heteroalkyl, cycloalkyl, heterocycloalkyl, aryl, heteroaryl, alkyl-aryl and alkyl-heteroaryl are optionally substituted with one or more substituents selected from the group consisting of $(C_1$-$C_{10})$-alkyl, $(C_1$-$C_{10})$-alkenyl, alkoxy, halo, hydroxy, $C(O)OR_{10}$, $NR_{11}R_{12}$, wherein $R_{10}$-$R_{12}$ are independently selected from the group consisting of hydrogen, $(C_1$-$C_{10})$-alkyl and $(C_1$-$C_{10})$-alkenyl; and wherein $R_8$ and $R_9$ are independently selected from the group consisting of hydrogen, alkyl and alkoxy, wherein $R_8$ and $R_9$ may optionally form a substituted or unsubstituted cyclic structure or ring; and wherein $E_1$ and $E_2$ are independently selected from the group consisting of $CR_{13}$, $C(R_{13})_2$, O, S and $NR_{14}$, wherein $R_{13}$ and $R_{14}$ are independently selected from the group consisting of hydrogen, alkyl, heteroalkyl, aryl and heteroaryl; and wherein $G_1$ and $G_2$ are independently selected from N and P; and wherein any two of $R_1$-$R_7$ that are vicinal to one another may optionally form a substituted or unsubstituted, saturated or unsaturated, cyclic structure or ring.

In some embodiments, $R_8$ and $R_9$ are selected to form an ester ring structure of a 4,4,5,5-tetramethyl-1,3,2-dioxaborolane (BPin) derivative and $R_1$-$R_4$ are selected to be alkyl. In such embodiments, the cobalt complex can have the following specific structures:

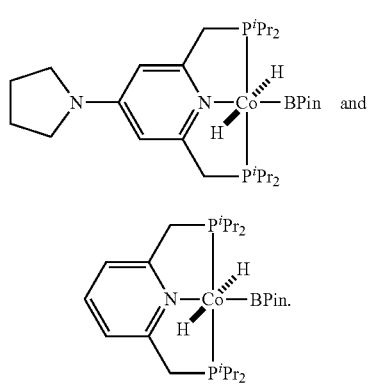

(Ia)

(Ib)

In another aspect a cobalt complex is of Formula (II):

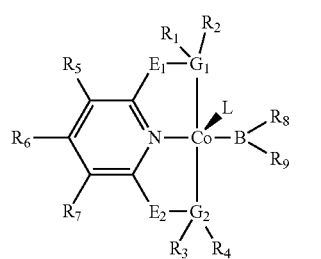

(II)

wherein $R_1$-$R_7$ are independently selected from the group consisting of hydrogen, alkyl, heteroalkyl, cycloalkyl, heterocycloalkyl, aryl, heteroaryl, alkyl-aryl and alkyl-heteroaryl, wherein the alkyl, heteroalkyl, cycloalkyl, heterocycloalkyl, aryl, heteroaryl, alkyl-aryl and alkyl-heteroaryl are optionally substituted with one or more substituents selected from the group consisting of $(C_1$-$C_{10})$-alkyl, $(C_1$-$C_{10})$-alkenyl, alkoxy, halo, hydroxy, $C(O)OR_{10}$, $NR_{11}R_{12}$, wherein $R_{10}$-$R_{12}$ are independently selected from the group consisting of hydrogen, $(C_1$-$C_{10})$-alkyl and $(C_1$-$C_{10})$-alkenyl; and wherein $R_8$ and $R_9$ are independently selected from the group consisting of hydrogen, alkyl and alkoxy, wherein $R_8$ and $R_9$ may optionally form a substituted or unsubstituted cyclic structure or ring; and wherein $E_1$ and $E_2$ are independently selected from the group consisting of $CR_{13}$, $C(R_{13})_2$, O, S and $NR_{14}$, wherein $R_{13}$ and $R_{14}$ are independently selected from the group consisting of hydrogen, alkyl, heteroalkyl, aryl and heteroaryl; and wherein $G_1$ and $G_2$ are independently selected from N and P; and wherein L is selected from the group consisting of $N_2$, CO, phosphine, tetrahydrofuran, amine, alkoxy and inert to electron donor ligand; and wherein any two of $R_1$-$R_7$ that are vicinal to one another may optionally form a substituted or unsubstituted, saturated or unsaturated, cyclic structure or ring.

In some embodiments, $R_8$ and $R_9$ are selected to form an ester ring structure of a 4,4,5,5-tetramethyl-1,3,2-dioxaborolane (BPin) derivative, $R_1$-$R_4$ are selected to be alkyl and L is selected to be $N_2$ or CO. In such embodiments, the cobalt complex can have the following specific structures:

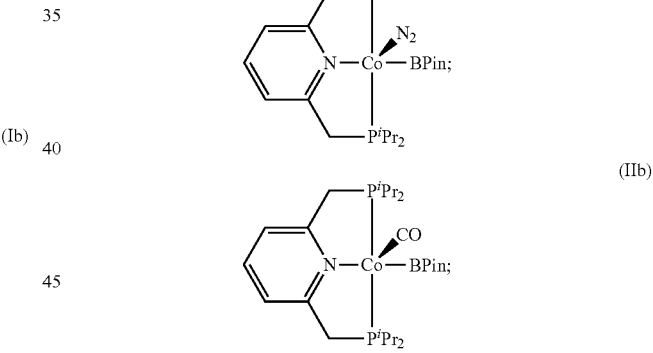

(IIa)

(IIb)

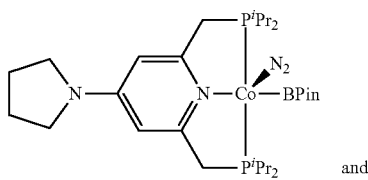

(IIIc)

and

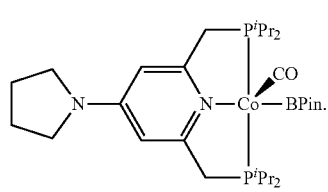

(IId)

In another aspect a cobalt complex is of Formula (III):

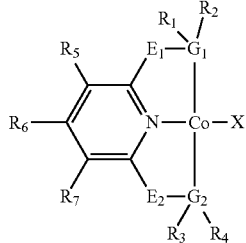
(III)

wherein $R_1$-$R_7$ are independently selected from the group consisting of hydrogen, alkyl, heteroalkyl, cycloalkyl, heterocycloalkyl, aryl, heteroaryl, alkyl-aryl and alkyl-heteroaryl, wherein the alkyl, heteroalkyl, cycloalkyl, heterocycloalkyl, aryl, heteroaryl, alkyl-aryl and alkyl-heteroaryl are optionally substituted with one or more substituents selected from the group consisting of $(C_1$-$C_{10})$-alkyl, $(C_1$-$C_{10})$-alkenyl, alkoxy, halo, hydroxy, $C(O)OR_{10}$, $NR_{11}R_{12}$, wherein $R_{10}$-$R_{12}$ are independently selected from the group consisting of hydrogen, $(C_1$-$C_{10})$-alkyl and $(C_1$-$C_{10})$-alkenyl; and wherein $E_1$ and $E_2$ are independently selected from the group consisting of $CR_8$, $C(R_8)_2$, O, S and $NR_9$, wherein $R_8$ and $R_9$ are independently selected from the group consisting of hydrogen, alkyl, heteroalkyl, aryl and heteroaryl; and wherein $G_1$ and $G_2$ are independently selected from N and P such that $G_1$ and $G_2$ are not both P; and wherein any two of $R_1$-$R_7$ that are vicinal to one another may optionally form a substituted or unsubstituted, saturated or unsaturated, cyclic structure or ring; and wherein X is selected from the group consisting of alkyl, heteroalkyl, aryl, heteroaryl, alkyl-aryl, alkyl-heteroaryl, aryl-alkyl, heteroaryl-alkyl, hydroxyl, alkoxy, halo, $R_{13}COO$— and —$B(R_{14})(R_{15})$, wherein $R^{13}$ is selected from the group consisting of alkyl, heteroalkyl, alkenyl, aryl and heteroaryl and $R_{14}$ and $R_{15}$ are independently selected from the group consisting of hydrogen, alkyl and alkoxy, wherein $R_{14}$ and $R_{15}$ may optionally form a substituted or unsubstituted cyclic structure or ring. In some embodiments, X is halo or BPin or $R_{13}COO$—, wherein $R_{13}$ is alkyl. Alternatively, X is heteroalkyl of formula

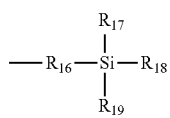

wherein $R_{16}$ is selected from the group consisting of alkyl, alkenyl, aryl, heteroaryl, alkyl-aryl, alkyl-heteroaryl, aryl-alkyl and heteroaryl-alkyl and $R_{17}$-$R_{19}$ are independently selected from the group consisting of hydrogen, alkyl, alkenyl, aryl, heteroaryl, alkyl-aryl, alkyl-heteroaryl, alkoxy and hydroxy. For example, in some embodiments, X is —$CH_2$—$Si(CH_3)_3$.

In some embodiments, $R_1$-$R_4$ are selected to be alkyl. In such embodiments, the cobalt complexes can have the specific structure:

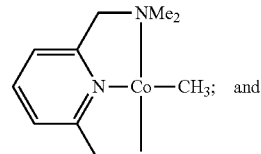
(IIIa)

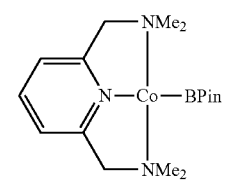
(IIIb)

In another aspect, a cobalt complex is of Formula (IV):

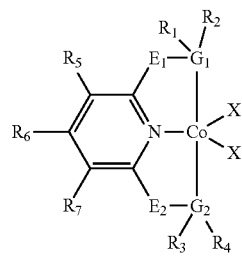
(IV)

wherein $R_1$-$R_7$ are independently selected from the group consisting of hydrogen, alkyl, heteroalkyl, cycloalkyl, heterocycloalkyl, aryl, heteroaryl, alkyl-aryl and alkyl-heteroaryl, wherein the alkyl, heteroalkyl, cycloalkyl, heterocycloalkyl, aryl, heteroaryl, alkyl-aryl and alkyl-heteroaryl are optionally substituted with one or more substituents selected from the group consisting of $(C_1$-$C_{10})$-alkyl, $(C_1$-$C_{10})$-alkenyl, alkoxy, halo, hydroxy, $C(O)OR_{10}$, $NR_{11}R_{12}$, wherein $R_{10}$-$R_{12}$ are independently selected from the group consisting of hydrogen, $(C_1$-$C_{10})$-alkyl and $(C_1$-$C_{10})$-alkenyl; and wherein $E_1$ and $E_2$ are independently selected from the group consisting of $CR_8$, $C(R_8)_2$, O, S and $NR_9$, wherein $R_8$ and $R_9$ are independently selected from the group consisting of hydrogen, alkyl, heteroalkyl, aryl and heteroaryl; and wherein $G_1$ and $G_2$ are independently selected from N and P; and wherein any two of $R_1$-$R_7$ that are vicinal to one another may optionally form a substituted or unsubstituted, saturated or unsaturated, cyclic structure or ring; and and wherein X is $R^{13}COO$—, where $R^{13}$ is selected from the group consisting of alkyl, heteroalkyl, alkenyl, aryl and heteroaryl. In some embodiments, wherein $G_1$ and $G_2$ are not each selected to be P, X is selected from the group consisting of halo and $R^{13}COO$—, where $R^{13}$ is selected from the group consisting of alkyl, heteroalkyl, alkenyl, aryl and heteroaryl.

In some embodiments, $R_1$-$R_4$ are selected to be alkyl. In such embodiments, cobalt complexes can have the following specific structures:

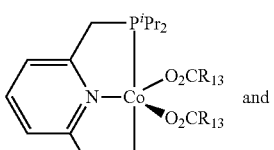

(IVa)

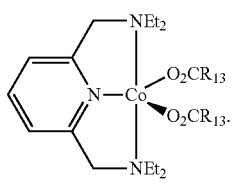

(IVb)

In another aspect, a cobalt complex is of Formula (V):

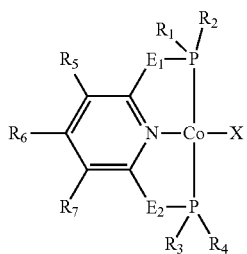

(V)

wherein $R_1$-$R_7$ are independently selected from the group consisting of hydrogen, alkyl, heteroalkyl, cycloalkyl, heterocycloalkyl, aryl, heteroaryl, alkyl-aryl and alkyl-heteroaryl, wherein the alkyl, heteroalkyl, cycloalkyl, heterocycloalkyl, aryl, heteroaryl, alkyl-aryl and alkyl-heteroaryl are optionally substituted with one or more substituents selected from the group consisting of ($C_1$-$C_{10}$)-alkyl, ($C_1$-$C_{10}$)-alkenyl, alkoxy, halo, hydroxy, C(O)O$R_{10}$, N$R_{11}R_{12}$, wherein $R_{10}$-$R_{12}$ are independently selected from the group consisting of hydrogen, ($C_1$-$C_{10}$)-alkyl and ($C_1$-$C_{10}$)-alkenyl; and wherein $E_1$ and $E_2$ are independently selected from the group consisting of C$R_8$, C($R_8$)$_2$, O, S and N$R_9$, wherein $R_8$ and $R_9$ are independently selected from the group consisting of hydrogen, alkyl, heteroalkyl, aryl and heteroaryl; and wherein any two of $R_1$-$R_7$ that are vicinal to one another may optionally form a substituted or unsubstituted, saturated or unsaturated, cyclic structure or ring; and wherein X is selected from the group consisting of heteroalkyl, aryl, heteroaryl, alkyl-aryl, alkyl-heteroaryl, arylalkyl, heteroaryl-alkyl, hydroxyl, alkoxy, halo, $R_{13}$COO— and —B($R_{14}$)($R_{15}$), wherein $R^{13}$ is selected from the group consisting of alkyl, heteroalkyl, alkenyl, aryl and heteroaryl and $R_{14}$ and $R_{15}$ are independently selected from the group consisting of hydrogen, alkyl and alkoxy, wherein $R_{14}$ and $R_{15}$ may optionally form a substituted or unsubstituted cyclic structure or ring. In some embodiments, X is chloro or BPin or $R_{13}$COO—, wherein $R_{13}$ is alkyl. Alternatively, X is heteroalkyl of formula

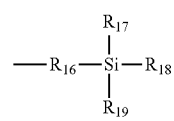

wherein $R_{16}$ is selected from the group consisting of alkyl, alkenyl, aryl, heteroaryl, alkyl-aryl, alkyl-heteroaryl, arylalkyl and heteroaryl-alkyl and $R_{17}$-$R_{19}$ are independently selected from the group consisting of hydrogen, alkyl, alkenyl, aryl, heteroaryl, alkyl-aryl, alkyl-heteroaryl, alkoxy and hydroxy. For example, in some embodiments, X is —CH$_2$—Si(CH$_3$)$_3$.

In some embodiments, $R_1$-$R_4$ are selected to be alkyl. In such embodiments, cobalt complexes can have the following specific structures:

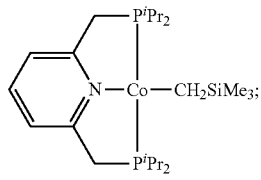

(Va)

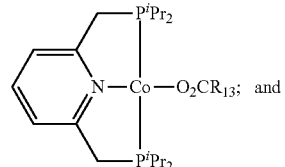

(Vb)

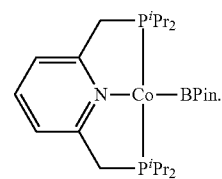

(Vc)

Moreover, in some embodiments, $E_1$ and $E_2$ are selected to include a heteroatom. In specific embodiments, $E_1$ and $E_2$ are selected to be —NH— yielding cobalt complexes of formulas:

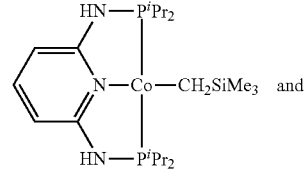

(Vd)

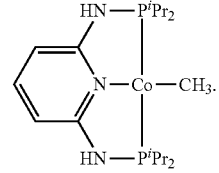

(Ve)

In further embodiments, a cobalt complex described herein is of Formula (VI):

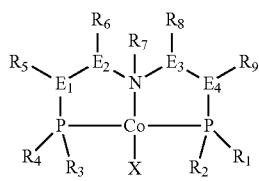

(VI)

wherein $R_1$-$R_9$ are independently selected from the group consisting of hydrogen, alkyl, heteroalkyl, cycloalkyl, heterocycloalkyl, aryl, heteroaryl, alkyl-aryl and alkyl-heteroaryl, wherein the alkyl, heteroalkyl, cycloalkyl, heterocycloalkyl, aryl, heteroaryl, alkyl-aryl and alkyl-heteroaryl are optionally substituted with one or more substituents selected from the group consisting of $(C_1$-$C_{10})$-alkyl, $(C_1$-$C_{10})$-alkenyl, alkoxy, halo, hydroxy, $C(O)OR_{13}$, $NR_{14}R_{15}$, wherein $R_{13}$-$R_{15}$ are independently selected from the group consisting of hydrogen, $(C_1$-$C_{10})$-alkyl and $(C_1$-$C_{10})$-alkenyl and wherein $R_5$-$R_9$ may form part of a cyclic or aromatic system; and wherein $E_1$-$E_4$ are independently selected from the group consisting or $C(R_{11})_2$, $C(R_{11})$ and $Si(R_{12})_2$, wherein $R_{11}$ and $R_{12}$ are independently selected from the group consisting of hydrogen, alkyl and aryl; and wherein X is selected from the group consisting of alkyl, heteroalkyl, aryl, heteroaryl, alkyl-aryl, alkyl-heteroaryl, aryl-alkyl, heteroaryl-alkyl, halo, hydroxy and alkoxy.

II. Methods of Borylation

In another aspect, methods of providing borylated products employing cobalt catalysts are described herein. For example, a method of providing a borylated product comprises providing a reaction mixture including an arene or aromatic heterocycle and a cobalt complex having a boron-containing ligand and reacting the arene or aromatic heterocycle with the boron containing ligand, wherein the cobalt complex is of Formula (I):

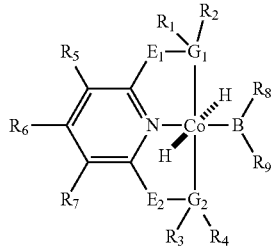

(I)

wherein $R_1$-$R_7$ are independently selected from the group consisting of hydrogen, alkyl, heteroalkyl, cycloalkyl, heterocycloalkyl, aryl, heteroaryl, alkyl-aryl and alkyl-heteroaryl, wherein the alkyl, heteroalkyl, cycloalkyl, heterocycloalkyl, aryl, heteroaryl, alkyl-aryl and alkyl-heteroaryl are optionally substituted with one or more substituents selected from the group consisting of $(C_1$-$C_{10})$-alkyl, $(C_1$-$C_{10})$-alkenyl, alkoxy, halo, hydroxy, $C(O)OR_{10}$, $NR_{11}R_{12}$, wherein $R_{10}$-$R_{12}$ are independently selected from the group consisting of hydrogen, $(C_1$-$C_{10})$-alkyl and $(C_1$-$C_{10})$-alkenyl; and wherein $R_8$ and $R_9$ are independently selected from the group consisting of hydrogen, alkyl and alkoxy, wherein $R_8$ and $R_9$ may optionally form a substituted or unsubstituted cyclic structure or ring; and wherein $E_1$ and $E_2$ are independently selected from the group consisting of $CR_{13}$, $C(R_{13})_2$, O, S and $NR_{14}$, wherein $R_{13}$ and $R_{14}$ are independently selected from the group consisting of hydrogen, alkyl, heteroalkyl, aryl and heteroaryl; and wherein $G_1$ and $G_2$ are independently selected from N and P; and wherein any two of $R_1$-$R_7$ that are vicinal to one another may optionally form a substituted or unsubstituted, saturated or unsaturated, cyclic structure or ring. In some embodiments, $R_8$ and $R_9$ are selected to form a cyclic boronate ester, such as BPin.

Arenes suitable for borylation according to the present method, in some embodiments, are six-membered arenes, including benzene and substituted benzenes. Substituted benzenes can include alkyl substituents, halo substituents, alkoxy substituents and various combinations thereof. Suitable arenes can also include various fused ring systems. Additionally, aromatic heterocycles suitable for borylation according to the present method include five-membered heterocycles and six-membered heterocycles. Five-membered aromatic heterocycles, in some embodiments, are substituted or unsubstituted pyrrole, furan, thiophene, imidazole and thiazole. Moreover, six-membered heterocycles can include substituted or unsubstituted pyridine and pyrimidine. Aromatic heterocycles suitable for borylation according to the present method can also comprise fused ring systems such as quinoline, isoquinoline, indole, purine and/or derivatives thereof.

In another aspect, a method of providing a borylated product comprises providing a reaction mixture including an arene or aromatic heterocycle and a cobalt complex having a boron-containing ligand and reacting the arene or aromatic heterocycle with the boron containing ligand, wherein the cobalt complex is of Formula (II):

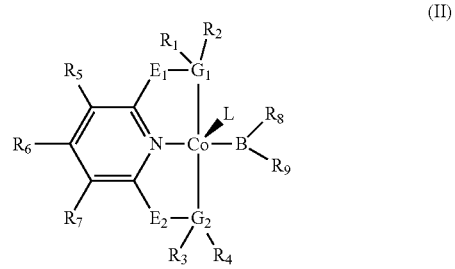

(II)

wherein $R_1$-$R_7$ are independently selected from the group consisting of hydrogen, alkyl, heteroalkyl, cycloalkyl, heterocycloalkyl, aryl, heteroaryl, alkyl-aryl and alkyl-heteroaryl, wherein the alkyl, heteroalkyl, cycloalkyl, heterocycloalkyl, aryl, heteroaryl, alkyl-aryl and alkyl-heteroaryl are optionally substituted with one or more substituents selected from the group consisting of $(C_1$-$C_{10})$-alkyl, $(C_1$-$C_{10})$-alkenyl, alkoxy, halo, hydroxy, $C(O)OR_{10}$, $NR_{11}R_{12}$, wherein $R_{10}$-$R_{12}$ are independently selected from the group consisting of hydrogen, $(C_1$-$C_{10})$-alkyl and $(C_1$-$C_{10})$-alkenyl; and wherein $R_8$ and $R_9$ are independently selected from the group consisting of hydrogen, alkyl and alkoxy, wherein $R_8$ and $R_9$ may optionally form a substituted or unsubstituted cyclic structure or ring; and wherein $E_1$ and $E_2$ are independently selected from the group consisting of $CR_{13}$, $C(R_{13})_2$, O, S and $NR_{14}$, wherein $R_{13}$ and $R_{14}$ are independently selected from the group consisting of hydrogen, alkyl, heteroalkyl, aryl and heteroaryl; and wherein $G_1$ and $G_2$ are independently selected from N and P; and wherein L is selected from the group consisting of $N_2$, CO, phosphine, amine, alkoxy, tetrahydrofuran and inert to electron donor ligand; and wherein any two of $R_1$-$R_7$ that are vicinal to one another may optionally form a substituted or unsubstituted, saturated or unsaturated, cyclic structure or ring. In some embodiments, $R_8$ and $R_9$ are selected to form a cyclic boronate ester, such as BPin. Arenes and aromatic heterocycles suitable for borylation in the presence of cobalt complexes of Formula (II) are consistent with the arenes and aromatic heterocycles described hereinabove for use with cobalt complexes of Formula (I).

In another aspect, a method of providing a borylated product comprises providing a reaction mixture including a cobalt complex, an arene or aromatic heterocycle and a borylation reagent and reacting the borylation reagent with the arene or aromatic heterocycle in the presence of the cobalt complex or a derivative thereof, the cobalt complex having Formula (III):

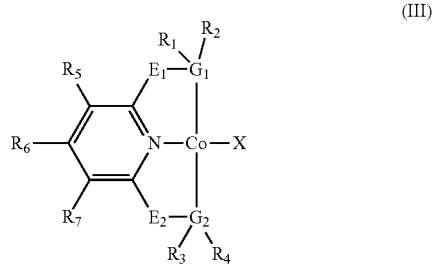
(III)

wherein $R_1$-$R_7$ are independently selected from the group consisting of hydrogen, alkyl, heteroalkyl, cycloalkyl, heterocycloalkyl, aryl, heteroaryl, alkyl-aryl and alkyl-heteroaryl, wherein the alkyl, heteroalkyl, cycloalkyl, heterocycloalkyl, aryl, heteroaryl, alkyl-aryl and alkyl-heteroaryl are optionally substituted with one or more substituents selected from the group consisting of ($C_1$-$C_{10}$)-alkyl, ($C_1$-$C_{10}$)-alkenyl, alkoxy, halo, hydroxy, C(O)O$R_{10}$, $NR_{11}R_{12}$, wherein $R_{10}$-$R_{12}$ are independently selected from the group consisting of hydrogen, ($C_1$-$C_{10}$)-alkyl and ($C_1$-$C_{10}$)-alkenyl; and wherein $E_1$ and $E_2$ are independently selected from the group consisting of $CR_8$, $C(R_8)_2$, O, S and $NR_9$, wherein $R_8$ and $R_9$ are independently selected from the group consisting of hydrogen, alkyl, heteroalkyl, aryl and heteroaryl; and wherein $G_1$ and $G_2$ are independently selected from N and P; and wherein any two of $R_1$-$R_7$ that are vicinal to one another may optionally form a substituted or unsubstituted, saturated or unsaturated, cyclic structure or ring; and wherein X is selected from the group consisting of alkyl, heteroalkyl, aryl, heteroaryl, alkyl-aryl, alkyl-heteroaryl, aryl-alkyl, heteroaryl-alkyl, hydroxyl, alkoxy, halo, $R_{13}$COO— and —B($R_{14}$)($R_{15}$), wherein $R^{13}$ is selected from the group consisting of alkyl, heteroalkyl, alkenyl, aryl and heteroaryl and $R_{14}$ and $R_{15}$ are independently selected from the group consisting of hydrogen, alkyl and alkoxy, wherein $R_{14}$ and $R_{15}$ may optionally form a substituted or unsubstituted cyclic structure or ring. In some embodiments, X is chloro or BPin or $R_{13}$COO—, wherein $R_{13}$ is alkyl. In some embodiments wherein X is —B($R_{14}$)($R_{15}$), the arene or aromatic heterocycle reacts with —B($R_{14}$)($R_{15}$) or a derivative thereof to provide the borylated product.

Alternatively, X is heteroalkyl of formula

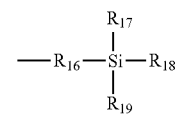

wherein $R_{16}$ is selected from the group consisting of alkyl, alkenyl, aryl, heteroaryl, alkyl-aryl, alkyl-heteroaryl, arylalkyl and heteroaryl-alkyl and $R_{17}$-$R_{19}$ are independently selected from the group consisting of hydrogen, alkyl, alkenyl, aryl, heteroaryl, alkyl-aryl, alkyl-heteroaryl, alkoxy and hydroxy. For example, in some embodiments, X is —$CH_2$—Si($CH_3$)$_3$. Arenes and aromatic heterocycles suitable for borylation in the presence of cobalt complexes of Formula (III) are consistent with the arenes and aromatic heterocycles described hereinabove for use with cobalt complexes of Formula (I).

Further, the borylation reagent can be a boronic acid derivative or a diboron compound. In some embodiments, for example, the borylation reagent is selected from the group consisting of 4,4,5,5-tetramethyl-1,3,2-dioxaborolane, 4,6,6-trimethyl-1,3,2-dioxaborinane, catecholborane, bis(pinacolato)diboron, bis(hexylene glycolato)diboron, bis(catecholato)diboron and bis(neopentyl glycolato)diboron.

In some embodiments, borylation according to the present method is conducted under neat conditions. Moreover, the amount of cobalt complex in the reaction mixture can vary depending on individual reaction parameters. In some embodiments, five-membered aromatic heterocycles require from 0.02 mol % to 1 mol. % cobalt complex. Six membered arenes can require higher loadings of cobalt complex ranging from 1 mol % to 3 mol %.

Cobalt complexes of Formula (III) can be air-sensitive. For example, exposure to air can oxidize the cobalt center leading to bis(phosphine) or bis(imine) ligand ejection. Therefore, the cobalt complexes are generally handled under inert conditions. Concomitantly, borylation reactions described herein can be performed under inert conditions.

In another aspect, a method of providing a borylated product comprises providing a reaction mixture including a cobalt complex, an arene or aromatic heterocycle and a borylation reagent and reacting the borylation reagent with the arene or aromatic heterocycle in the presence of the cobalt complex or a derivative thereof, the cobalt complex having Formula (IV):

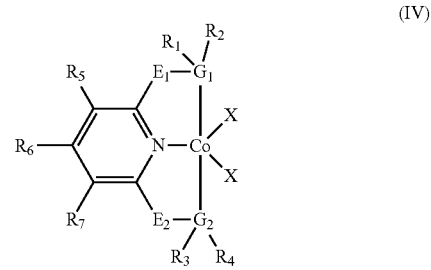
(IV)

wherein $R_1$-$R_7$ are independently selected from the group consisting of hydrogen, alkyl, heteroalkyl, cycloalkyl, heterocycloalkyl, aryl, heteroaryl, alkyl-aryl and alkyl-heteroaryl, wherein the alkyl, heteroalkyl, cycloalkyl, heterocycloalkyl, aryl, heteroaryl, alkyl-aryl and alkyl-heteroaryl are optionally substituted with one or more substituents selected from the group consisting of ($C_1$-$C_{10}$)-alkyl, ($C_1$-$C_{10}$)-alkenyl, alkoxy, halo, hydroxy, C(O)O$R_{10}$, N$R_{11}R_{12}$, wherein $R_{10}$-$R_{12}$ are independently selected from the group consisting of hydrogen, ($C_1$-$C_{10}$)-alkyl and ($C_1$-$C_{10}$)-alkenyl; and wherein $E_1$ and $E_2$ are independently selected from the group consisting of $CR_8$, C($R_8$)$_2$, O, S and N$R_9$, wherein $R_8$ and $R_9$ are independently selected from the group consisting of hydrogen, alkyl, heteroalkyl, aryl and heteroaryl; and wherein $G_1$ and $G_2$ are independently selected from N and P; and wherein any two of $R_1$-$R_7$ that are vicinal to one another may optionally form a substituted or unsubstituted, saturated or unsaturated, cyclic structure or ring; and and wherein X is selected from the group consisting of halo and $R^{13}$COO—, where $R^{13}$ is selected from the group consisting of alkyl, heteroalkyl, alkenyl, aryl and heteroaryl. Further, in some embodiments, wherein X is selected as halo, the reaction mixture further comprises an activator operable for activating the cobalt complex for catalysis. In such embodiments, the arene or aromatic heterocycle is reacted with the borylation reagent in the presence of the activated cobalt complex or a derivative of the activated cobalt complex. Suitable activator, in some embodiments, includes lithium methoxide (LiOMe). Further, in some embodiments, cobalt complexes of Formula (IV) are not sensitive to air permitting use under ambient conditions.

Arenes and aromatic heterocycles suitable for borylation in the presence of cobalt complexes of Formula (IV) are consistent with the arenes and aromatic heterocycles described hereinabove for use with cobalt complexes of Formula (I). Similarly, borylation reagents described hereinabove can also be suitable for use with cobalt complexes of Formula (IV).

In a further aspect, a method of providing a borylated product comprises providing a reaction mixture including a cobalt complex, an arene or aromatic heterocycle and a borylation reagent and reacting the borylation reagent with the arene or aromatic heterocycle in the presence of the cobalt complex or a derivative thereof, the cobalt complex having Formula (VI):

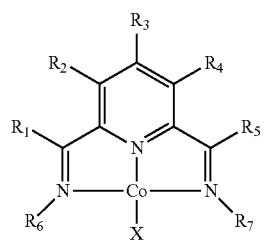

(VI)

wherein $R_1$-$R_7$ are independently selected from the group consisting of hydrogen, alkyl, heteroalkyl, cycloalkyl, heterocycloalkyl, aryl, heteroaryl, alkyl-aryl and alkyl-heteroaryl, wherein the alkyl, heteroalkyl, cycloalkyl, heterocycloalkyl, aryl, heteroaryl, alkyl-aryl and alkyl-heteroaryl are optionally substituted with one or more substituents selected from the group consisting of ($C_1$-$C_{10}$)-alkyl, ($C_1$-$C_{10}$)-alkenyl, alkoxy, halo, hydroxy, C(O)O$R_8$, N$R_9R_{10}$, wherein $R_8$-$R_{10}$ are independently selected from the group consisting of hydrogen, ($C_1$-$C_{10}$)-alkyl and ($C_1$-$C_{10}$)-alkenyl and wherein X is selected from the group consisting of alkyl, heteroalkyl, aryl, heteroaryl, alkyl-aryl, alkyl-heteroaryl, aryl-alkyl, heteroaryl-alkyl, hydroxy and alkoxy.

Arenes and aromatic heterocycles suitable for borylation in the presence of cobalt complexes of Formula (II) are consistent with the arenes and aromatic heterocycles described hereinabove for use with cobalt complexes of Formula (I). Similarly, borylation reagents described hereinabove can also be suitable for use with cobalt complexes of Formula (II).

These and other embodiments are further illustrated by the following non-limiting examples.

Example 1—Preparation of Cobalt Pyridine(Bisphosphine) Complex

Step I. A 100 ml round flask was charged with 0.500 g (1.07 mmol) of pyridine bis(diisopropylphosphine) cobalt dichloride in 30 mL of toluene. The purple suspension was frozen in a cold well and 1.07 ml of a 1.0M NaEt$_3$BH solution in toluene (1.07 mmol) was added via microsyringe to the thawing solution. The solution was allowed to stir for 18 h, turning brownish-purple after 2 h. Insolubles were removed via filtration through Celite, and the volatiles were removed under vacuum. Recrystallization of the dark residue from toluene/pentane (1:7) at −35° C. for 18 h afforded analytically pure dark purple crystals of pyridine bis(diisopropylphosphine) cobalt monochloride for use in subsequent Co complex preparation.

Step II. A 20 ml scintillation vial was charged with 0.150 g (0.346 mmol) of pyridine bis(diisopropylphosphine) cobalt monochloride and 5 ml of diethyl ether. The purple solution was chilled in a freezer to −35° C. A solution of 0.033 g (0.346 mmol) of neosilyl lithium in 5 ml of diethyl ether was added to the warming solution and a color change from dark purple to brown was observed. The solution was stirred for 1 h at room temperature before the volatiles were removed under vacuum, and the residue was extracted into 5 ml of toluene and filtered through Celite. Concentration of the filtrate under vacuum and recrystallization of the dark residue from diethyl ether at −35° C. afforded analytically pure dark brown crystals of pyridine bis(diisopropylphosphine) cobalt trimethylsilylmethane.

Example 2—Preparation of 4-pyrr-($^{iPr}$PNP)CoH$_2$(BPin)

4-pyrr-($^{iPr}$PNP)CoH$_2$(BPin) was prepared according to the following reaction schemes and protocols of Methods A and B:

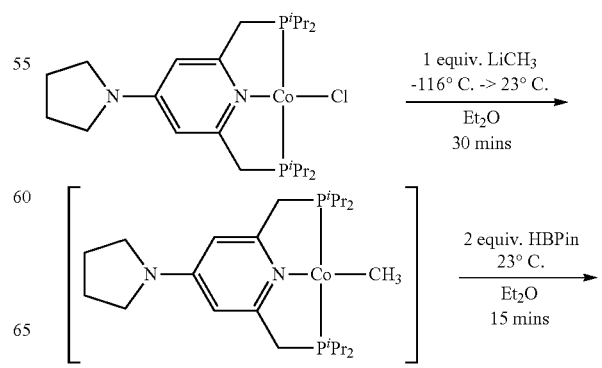

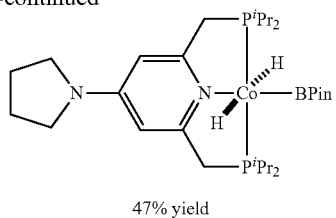

47% yield

Method A.

A 100 mL round bottom flask was charged with 4-pyrr-($^{iPr}$PNP)CoCl (0.300 g, 0.597 mmol) and 40 mL of diethyl ether. In a separate vial, 1.6 M CH$_3$Li solution in diethyl ether (0.373 mL, 0.597 mmol) was additionally diluted with 10 mL of diethyl ether. The round bottom flask containing the 4-pyrr-($^{iPr}$PNP)CoCl and the vial containing the CH$_3$Li were chilled in the cold well filled with liquid nitrogen for 20 minutes. The cold solution of CH$_3$Li was then added dropwise to the cold, stirring solution of the 4-pyrr-($^{iPr}$PNP)CoCl in diethyl ether. A color change from brown to purple was observed upon addition of CH$_3$Li. The reaction mixture was allowed to warm to room temperature, stirred for an additional 30 minutes and then filtered through a glass frit. An aliquot of the reaction mixture was taken and was concentrated in vacuo for ~30 seconds and was immediately analyzed via $^1$H NMR spectroscopy and the cobalt compound was identified as 4-pyrr-($^{iPr}$NP)CoCH$_3$ via $^1$H NMR spectroscopy. Special care must be taken upon handling the compound as it decomposes when exposed to vacuum.

$^1$H NMR (benzene-d$_6$, 23° C.): δ −0.77 (apparent triplet, $^3J_{PH}$=8.5, 3H, Co-Me), 1.31-1.38 (overlapping multiplets, 16H, P—CHMe$_2$ and NCH$_2$CH$_2$), 1.49 (m, 12H, P—CHMe$_2$), 2.29 (m, 4H, P—CHMe$_2$), 2.38 (bs, 4H, P—CH$_2$), 2.54 (m, NCH$_2$CH$_2$), 5.58 (s, meta pyridine CH). To the diethyl ether solution of 4-pyrr-($^{iPr}$PNP)CoCH$_3$, pinacolborane (0.153 g, 1.20 mmol) was added in one portion and an immediate color change to brownish yellow was observed. The solution was stirred for 15 minutes and the solvent was evaporated in vacuo. The resulting brown residue was recrystallized in a ~9:1 pentane:ether mixture to yield of 4-pyrr-($^{iPr}$PNP)CoH$_2$(BPin) (0.167 g, 47% yield) as a yellow powder.

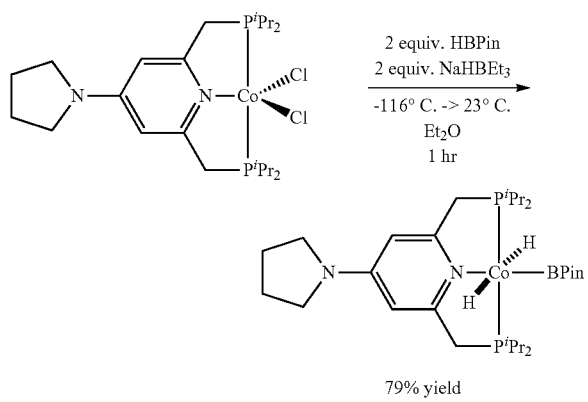

79% yield

Method B.

A 100 mL round bottom flask was charged with 4-pyrr-($^{iPr}$PNP)CoCl$_2$ (0.300 g, 0.557 mmol), 40 mL of diethyl ether, and pinacolborane (0.143 g, 1.117 mmol). To the stirring suspension was added a 1.0 M solution of NaHBEt$_3$ in toluene (1.114 mL, 1.114 mmol) at 23° C. The resulting yellow brown solution was stirred for 1 hour, was filtered through a pad of Celite and then evaporated in vacuo. The resulting brownish residue was recrystallized in pentane to yield 4-pyrr-($^{iPr}$PNP)CoH$_2$(BPin) (0.264 g, 79% yield) as a yellow powder. Recrystallization of the yellow powder from diethyl ether afforded crystals suitable for X-ray diffraction.

Anal Calcd for C$_{29}$H$_6$BCoN$_2$O$_2$P$_2$: C, 58.40; H, 9.46; N, 4.70. Found: C, 58.30; H, 9.58; N, 4.71.

$^1$H NMR (benzene-d$_6$, 23° C.): δ −9.03 (apparent triplet, $^2J_{PH}$=43.4, 2H, Co—H), 1.14-1.26 (overlapped singlet and multiplet, 24H, pinacol Me and P—CHMe$_2$), 1.39 (m, 4H, NCH$_2$CH$_2$), 1.60 (m, 12H, P—CHMe$_2$), 2.52 (br m, 4H, P—CHMe$_2$), 2.72 (m, 4H, NCH$_2$CH$_2$), 3.01 (br s, 4H, P—CH$_2$), 5.95 (s, 2H, meta pyridine CH).

{$^1$H}$^{13}$C NMR (benzene-d$_6$, 23° C.): δ 17.79 (P—CHMe$_2$), 19.90 (P—CHMe$_2$), 24.49 (t, J$_{PC}$=12, P—CHMe$_2$), 25.23 (NCH$_2$CH$_2$), 25.54 (pinacol Me), 38.74 (t, J$_{PC}$=7.6, P—CH$_2$), 46.84 (NCH$_2$CH$_2$), 79.42 (pinacol C), 102.44 (t, J$_{PC}$=4.2, meta pyridine CH), 150.04 (para pyridine C), 160.64 (ortho pyridine C).

{$^1$H}$^{31}$P NMR (benzene-d$_6$, 23° C.): δ 104.09 (br s, P—CHMe$_2$).

Example 3—Preparation of 4-pyrr-($^{iPr}$PNP)CoN$_2$(BPin)

4-pyrr-($^{iPr}$PNP)CoN$_2$(BPin) was prepared according to the following reaction scheme and protocol.

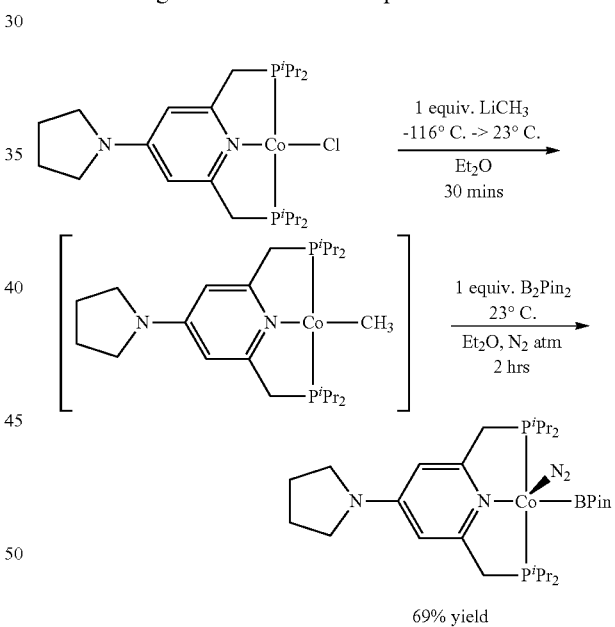

69% yield

A 100 mL round bottom flask was charged with 4-pyrr-($^{iPr}$PNP)CoCl (0.220 g, 0.437 mmol) and 30 mL of diethyl ether. In a separate vial, 1.6 M CH$_3$Li solution in diethyl ether (0.273 mL, 0.437 mmol) was additionally diluted with 10 mL of diethyl ether. The round bottom flask containing the 4-pyrr-($^{iPr}$PNP)CoCl and the vial containing the CH$_3$Li were chilled in the cold well filled with liquid nitrogen for 20 minutes. The cold solution of CH$_3$Li was then added dropwise to the cold, stirring solution of the 4-pyrr-($^{iPr}$PNP)CoCl in diethyl ether. A color change from brown to purple was observed upon addition of CH$_3$Li. The reaction mixture was allowed to warm to room temperature, stirred for an additional 30 minutes and then filtered through a glass frit.

To the diethyl ether solution of 4-pyrr-($^{iPr}$PNP)CoCH$_3$, bis(pinacolato)diboron (0.111 g, 0.437 mmol) in 5 mL of diethyl ether was added and the solution was stirred for 30 minutes. A color change from purple to dark red was observed. The solvent was evaporated in vacuo. The resulting brownish red residue was recrystallized in a ~9:1 pentane:ether mixture to yield of 4-pyrr-($^{iPr}$pNP)CoN$_2$(BPin) (0.187 g, 69% yield) as a red powder. Recrystallization of the red powder from diethyl ether afforded crystals suitable for X-ray diffraction. The red powder was dissolved in benzene-d$_6$ and was immediately analyzed by 2D NMR spectroscopy since the compound reacts with benzene-d$_6$ in the course of 24 hours. In THF-ds, however, the compound is stable up to 4 days without any evidence of decomposition.

Anal Calcd for C$_{29}$H$_{54}$BCoN$_4$O$_2$P$_2$: C, 55.96; H, 8.74; N, 9.00. Found: C, 55.73; H, 8.56; N, 8.45.

$^1$H NMR (benzene-d$_6$, 23° C.): δ 1.14 (br m, 12H, P—CHMe$_2$), 1.26 (s, 12H, pinacol Me), 1.36 (m, 4H, NCH$_2$CH$_2$), 1.56 (br m, 12H, P—CHMe$_2$), 2.41 (br m, 4H, P—CHMe$_2$), 2.69 (m, 4H, NCH$_2$CH$_2$), 3.09 (br s, 4H, P—CH$_2$), 5.93 (s, 2H, meta pyridine CH).

{$^1$H}$^{13}$C NMR (benzene-d$_6$, 23° C.): δ 18.89 (P—CHMe$_2$), 19.55 (P—CHMe$_2$), 25.23 (NCH$_2$CH$_2$), 26.10 (pinacol Me), 27.46 (P—CHMe$_2$), 39.77 (t, J$_{PC}$=5.0, P—CH$_2$), 46.87 (NCH$_2$CH$_2$), 79.81 (pinacol C), 102.53 (t, J$_{PC}$=3.6, meta pyridine CH), 150.45 (para pyridine C), 160.41 (ortho pyridine C).

{$^1$H}$^{31}$P NMR (benzene-d$_6$, 23° C.): δ 67.93 (s, P—CHMe$_2$).

$^1$H NMR (THF-ds, 23° C.): δ 0.95 (br m, 12H, P—CHMe$_2$), 1.04 (s, 12H, pinacol Me), 1.23 (br m, 12H, P—CHMe$_2$), 1.92 (m, 4H, NCH$_2$CH$_2$), 2.25 (br m, 4H, P—CHMe$_2$), 3.12 (br s, 4H, P—CH$_2$), 3.18 (m, 4H, NCH$_2$CH$_2$), 6.25 (s, 2H, meta pyridine CH).

{$^1$H}$^{13}$C NMR (THF-ds, 23° C.): δ 19.09 (P—CHMe$_2$), 19.86 (P—CHMe$_2$), 26.27 (NCH$_2$CH$_2$), 26.30 (pinacol Me), 28.10 (P—CHMe$_2$), 40.14 (t, J$_{PC}$=4.9, P—CH$_2$), 47.96 (NCH$_2$CH$_2$), 80.20 (pinacol C), 103.16 (t, J$_{PC}$=3.8, meta pyridine CH), 151.78 (para pyridine C), 161.05 (ortho pyridine C).

{$^1$H}$^{31}$P NMR (THF-ds, 23° C.): δ 67.23 (s, P—CHMe$_2$).

Example 4—Preparation of ($^{iPr}$PNP)CoOAc$_2$

A scintillation vial was charged with a stirbar, cobalt diacetate (0.200 g, 1.13 mmol) and 10 mL of tetrahydrofuran. To this stirring suspension was added ($^{iPr}$PNP) (0.383 g, 1.30 mmol). The solution was stirred at room temperature for 16 hours before the volatiles were removed in vacuo. The resulting purple solid was collected on a sintered glass frit to afford ($^{iPr}$PNP)CoOAc$_2$ as an analytically pure purple powder.

Example 5—Preparation of ($^{iPr}$NNN)CoCl$_2$ ($^{iPr}$NNN)CoCl$_2$ was prepared by the following reaction scheme and protocol.

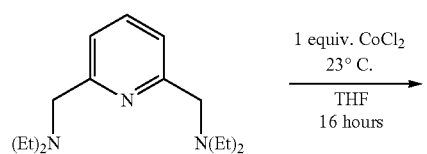

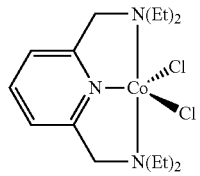

53% yield

A 50 mL round bottom flask was charged with a stirbar, cobalt dichloride (0.208 g, 1.60 mmol) and 30 mL of tetrahydrofuran. To this stirring suspension was added ($^{Et}$NNN) (0.400 g, 1.60 mmol). The solution was stirred at room temperature for 16 hours before the volatiles were removed in vacuo. The resulting light blue solid was collected on a sintered glass frit to afford ($^{Et}$NNN)CoCl$_2$ (0.321 g, 53% yield) as an analytically pure light purple powder.

Example 6—Borylation of Aromatic Five-Membered Heterocycle

A scintillation vial (with a magnetic stir bar) was charged with bis(diisopropylphosphine) cobalt dichloride (0.03 mmol), 2 methylfuran (1 mmol) and pinacolborane (1 mmol), LiOMe (0.06 mmol) and 1 mL of THF. The reaction was monitored by the analysis of an aliquot of the mixture by GC-FID. The mixture was allowed to stir to completion at room temperature and was quenched by exposure to air. The resulting solid was solubilized in CDCl$_3$, passed through a plug of silica gel in a Pasteur pipette and then analyzed by $^1$H and $^{13}$C NMR spectroscopy without further purification.

Example 7—Borylation of Aromatic Six-Membered Heterocycle

A scintillation vial (with a magnetic stir bar) was charged with bis(diisopropylphosphine) cobalt dichloride (0.03 mmol), 2,6-lutidine (1 mmol) and bispinacolatodiboron [B$_2$Pin$_2$](1 mmol), LiOMe (0.06 mmol) and 1 mL of THF. The reaction was heated to 80° C. for 24 hours and was quenched by exposure to air. The resulting solid was solubilized in CDCl$_3$, passed through a plug of silica gel in a Pasteur pipette and then analyzed by 'H and'$^3$C NMR spectroscopy without further purification.

Example 8—Borylation of Aromatic Five-Membered Heterocycle

A scintillation vial (with a magnetic stir bar) was charged with bis(diisopropylphosphine) cobalt diacetate (0.05 mmol), benzofuran (1 mmol) and pinacolborane (1 mmol), and 1 mL of THF. The reaction was monitored by the analysis of an aliquot of the mixture by GC-FID. The mixture was allowed to stir to completion at room temperature and was quenched by exposure to air. The resulting solid was solubilized in CDCl$_3$, passed through a plug of silica gel in a Pasteur pipette and then analyzed by $^1$H and $^{13}$C NMR spectroscopy without further purification.

Example 9—Borylation of Aromatic Five-Membered Heterocycle

Figure 2:
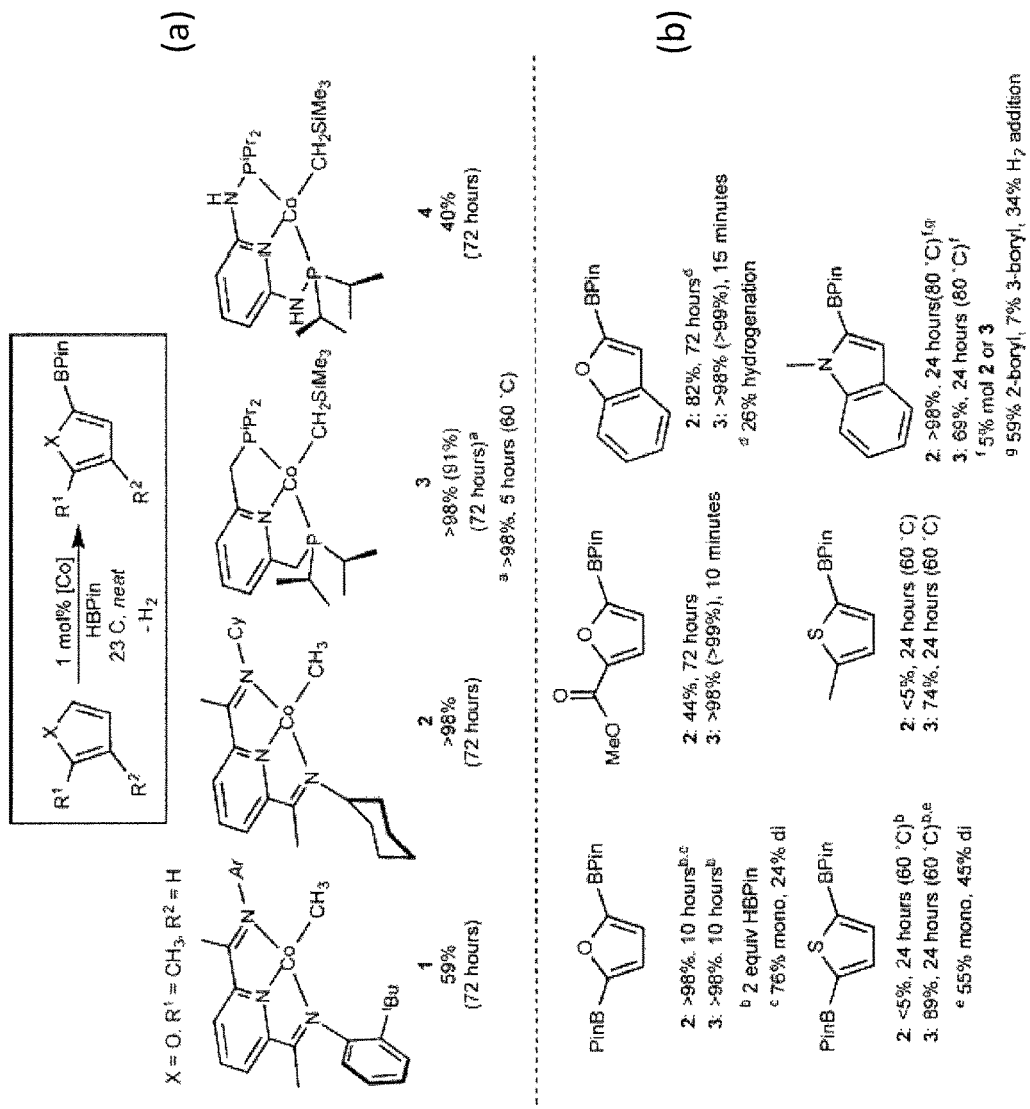
FIGS. 2(a)-(b) illustrate borylation of five-membered aromatic heterocycles in the presence of cobalt complexes described herein.

According to the reaction scheme illustrated in FIG. 2(a), a scintillation vial (with a magnetic stir bar) was charged with cobalt complex (0.01 mmol) selected from 1-4, 2 methylfuran (1 mmol) and pinacolborane (1 mmol). The reaction was monitored by the analysis of an aliquot of the mixture by GC-FID. The mixture was allowed to stir to completion at room temperature and was quenched by exposure to air. The resulting solid was solubilized in $CDCl_3$, passed through a plug of silica gel in a Pasteur pipette and then analyzed by $^1H$ and $^{13}C$ NMR spectroscopy without further purification. If desired, the foregoing reaction can also be administered in 2 ml of tetrahydrofuran (THF). FIG. 2(a) provides conversion percentages for cobalt complexes 1-4 with values in parenthesis as isolated yields. Further, FIG. 2(b) details additional borylation products achieved with Co complexes 2 and 3 according to the foregoing reaction parameters.

Example 10—Borylation of Aromatic Six-Membered Heterocycle

Figure 3:
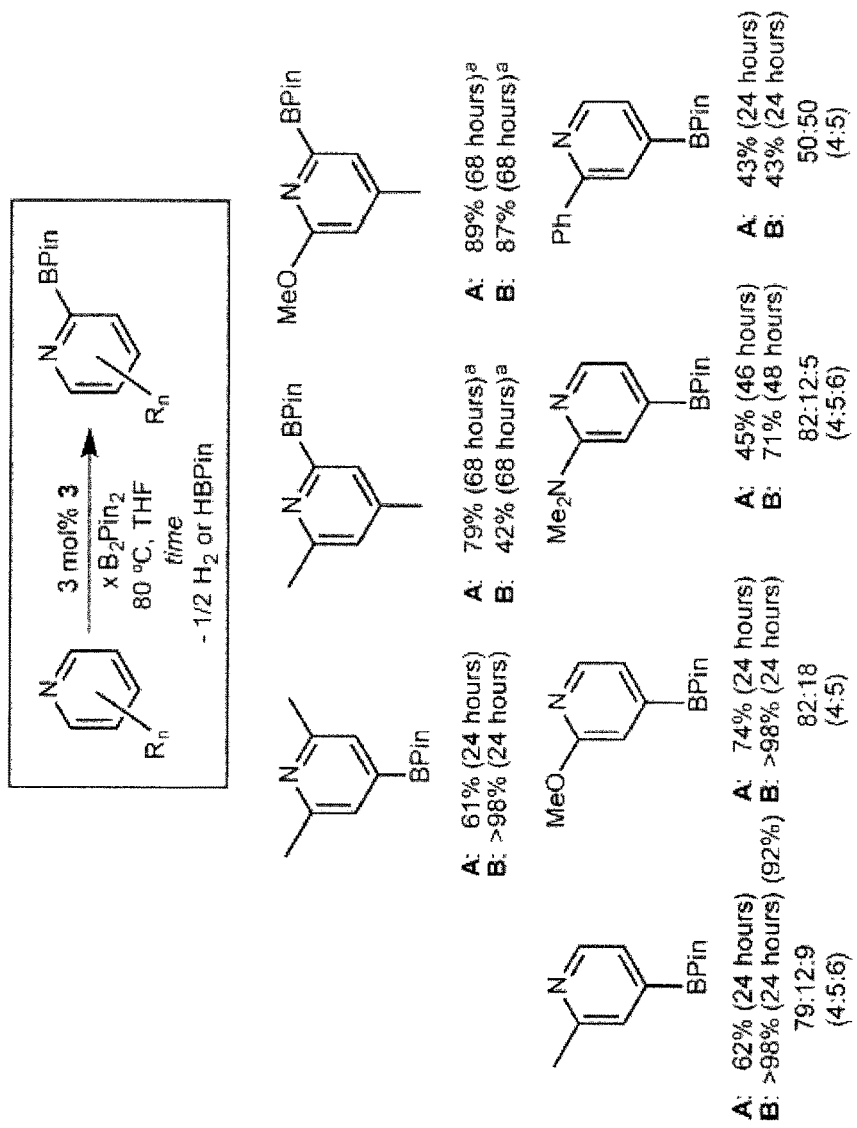
FIG. 3 illustrates borylation of six membered aromatic heterocycles in the presence of a cobalt complex according to some embodiments described herein.

According to the reaction scheme illustrated in FIG. 3, various pyridines underwent borylation with bis(pinacolato) diboron [$B_2Pin_2$] in the presence of bis(diisopropylphosphine) cobalt trimethylsilylmethane. Condition A employed 0.5 equiv. of $B_2Pin_2$ and Condition B employed 1.0 equiv. of $B_2Pin_2$. Reported numbers are percent conversions of the corresponding pyridine derivative determined by GC analysis using mesitylene as an internal standard. Values in parenthesis are isolated yield. Product ratios were determined by NMR analysis. Values under the percent conversions are selectivities, and the number in parenthesis denote the position of borylation. Selectivities were the same for Conditions A and B.

Example 11—Borylation of Six-Membered Arene

Figure 4:
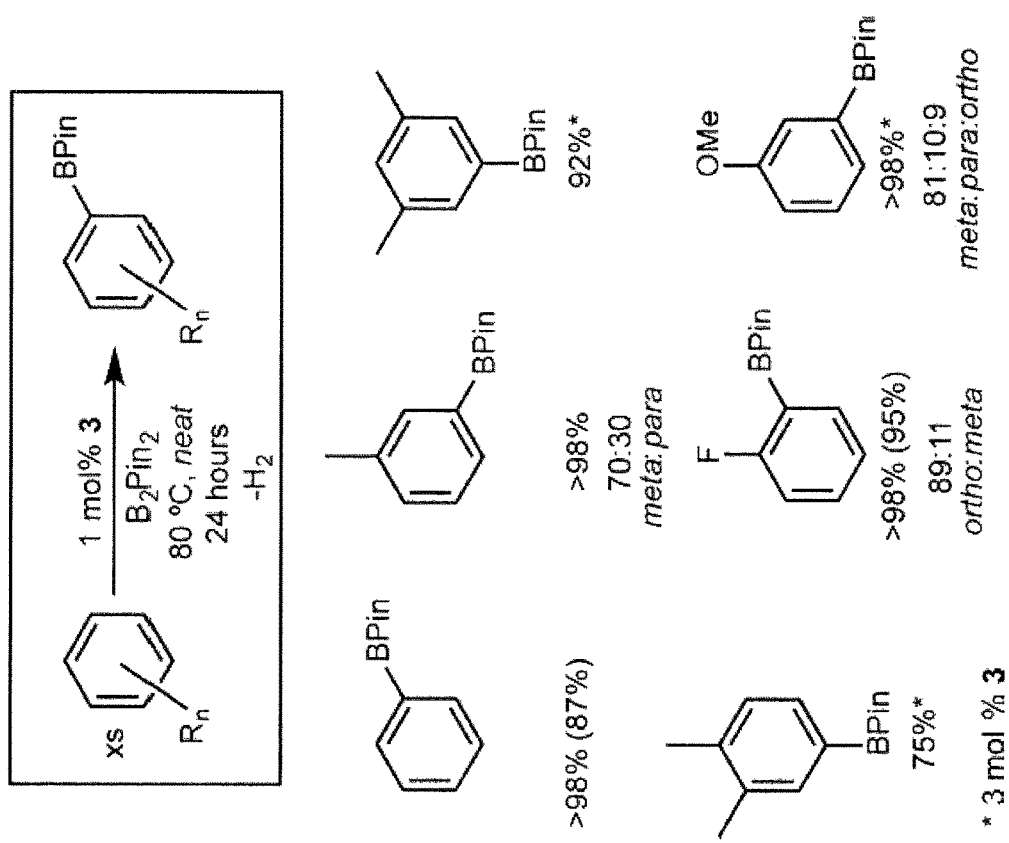
FIG. 4 illustrates borylation of arenes in the presence of a cobalt complex according to some embodiments described herein.

According to the reaction scheme illustrated in FIG. 4, benzene and various benzene derivatives underwent borylation with $B_2Pin_2$ in the presence of bis(diisopropylphosphine) cobalt trimethylsilylmethane. A scintillation vial (with a magnetic stir bar) was charged with bis(diisopropylphosphine) cobalt trimethylsilylmethane (0.015 mmol), benzene or benzene derivative (5 mmol) and $B_2Pin_2$. The resulting reaction mixture was allowed to stir at 80° C. in an oil bath for 24 h and was quenched by exposing the mixture to air. The mixture was solubilized in $CDCl_3$, passed through a plug of silica gel in a Pasteur pipette and then analyzed by $^1H$ and $^{13}C$ NMR spectroscopy without further purification. Reported values are percent conversions of $B_2Pin_2$ determined by GC using mesitylene as an internal standard. Product ratios were determined by NMR analysis. Isolated yields are reported in parenthesis.

Example 12—Borylation of Aromatic Five-Membered Heterocycle

A scintillation vial (with a magnetic stir bar) was charged with 4-pyrr-bis(diisopropylphosphine) cobalt dihydride boryl (0.03 mmol), 2 methylfuran (1 mmol) and pinacolborane (1 mmol), and 1 mL of THF. The reaction was monitored by the analysis of an aliquot of the mixture by GC-FID. The mixture was allowed to stir to completion at room temperature and was quenched by exposure to air. The resulting solid was solubilized in $CDCl_3$, passed through a plug of silica gel in a Pasteur pipette and then analyzed by $^1H$ and $^{13}C$ NMR spectroscopy without further purification.

Example 13—Borylation of Aromatic Six-Membered Heterocycle

A scintillation vial (with a magnetic stir bar) was charged with 4-pyrr-bis(diisopropylphosphine) cobalt dihydride boryl (0.03 mmol), 2,6-lutidine (1 mmol) and bispinacolatodiboron (1 mmol), and 1 mL of THF. The reaction was heated to 80° C. for 24 hours and was quenched by exposure to air. The resulting solid was solubilized in $CDCl_3$, passed through a plug of silica gel in a Pasteur pipette and then analyzed by $^1H$ and $^{13}C$ NMR spectroscopy without further purification.

Example 14—Borylation of Six-Membered Arene

A scintillation vial (with a magnetic stir bar) was charged with 4-pyrr-bis(diisopropylphosphine) cobalt dihydride boryl (0.03 mmol), benzene (1 mmol) and bispinacolatodiboron (1 mmol), and 1 mL of THF. The reaction was heated to 80° C. for 24 hours and was quenched by exposure to air. The resulting solid was solubilized in $CDCl_3$, passed through a plug of silica gel in a Pasteur pipette and then analyzed by $^1H$ and $^{13}C$ NMR spectroscopy without further purification.

Example 15:—Borylation of Aromatic Five-Membered Heterocycle

A scintillation vial (with a magnetic stir bar) was charged with 4-pyrr-bis(diisopropylphosphine) cobalt dinitrogen boryl (0.03 mmol), 2 methylfuran (1 mmol) and pinacolborane (1 mmol), and 1 mL of THF. The reaction was monitored by the analysis of an aliquot of the mixture by GC-FID. The mixture was allowed to stir to completion at room temperature and was quenched by exposure to air. The resulting solid was solubilized in $CDCl_3$, passed through a plug of silica gel in a Pasteur pipette and then analyzed by $^1H$ and $^{13}C$ NMR spectroscopy without further purification.

Example 16—Borylation of Aromatic Six-Membered Heterocycle

A scintillation vial (with a magnetic stir bar) was charged with 4-pyrr-bis(diisopropylphosphine) cobalt dinitrogen boryl (0.03 mmol), 2,6-lutidine (1 mmol) and bispinacolatodiboron (1 mmol), and 1 mL of THF. The reaction was heated to 80° C. for 24 hours and was quenched by exposure to air. The resulting solid was solubilized in $CDCl_3$, passed through a plug of silica gel in a Pasteur pipette and then analyzed by $^1H$ and $^{13}C$ NMR spectroscopy without further purification.

Example 17—Borylation of Six-Membered Arene

A scintillation vial (with a magnetic stir bar) was charged with 4-pyrr-bis(diisopropylphosphine) cobalt dinitrogen boryl (0.03 mmol), benzene (1 mmol) and bispinacolatodiboron (1 mmol), and 1 mL of THF. The reaction was heated to 80° C. for 24 hours and was quenched by exposure to air. The resulting solid was solubilized in $CDCl_3$, passed through a plug of silica gel in a Pasteur pipette and then analyzed by '$H$ and'$^3C$ NMR spectroscopy without further purification.

Various embodiments of the invention have been described in fulfillment of the various objects of the invention. It should be recognized that these embodiments are merely illustrative of the principles of the present invention.

Numerous modifications and adaptations thereof will be readily apparent to those skilled in the art without departing from the spirit and scope of the invention.

The invention claimed is:

1. A cobalt complex is of Formula (IV):

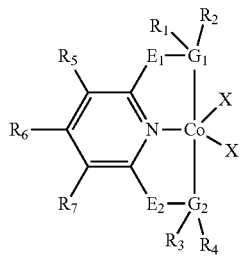

wherein $R_1$-$R_4$ are independently selected from the group consisting of hydrogen and alkyl, and wherein $R_5$-$R_7$ are independently selected from the group consisting of hydrogen, alkyl, and heteroalkyl; and
wherein $E_1$ and $E_2$ are independently selected from the group consisting of $CR_8$, and $C(R_8)_2$, wherein $R_8$ is selected from the group consisting of hydrogen, and alkyl; and
wherein $G_1$ and $G_2$ are independently selected from N and P; and
and
and wherein X is $R^{13}COO-$, where $R^{13}$ is alkyl.

2. The cobalt complex of Formula (IV), wherein $G_1$ and $G_2$ are not each P.

3. The cobalt complex of claim 1, wherein $R_1$-$R_4$ are independently alkyl.

4. The cobalt complex of claim 3 having the structure:

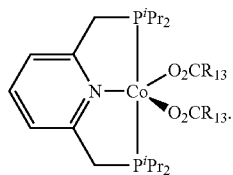

5. The cobalt complex of claim 3, having the structure:

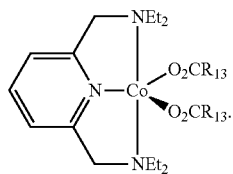

6. A cobalt complex is of Formula (IV):

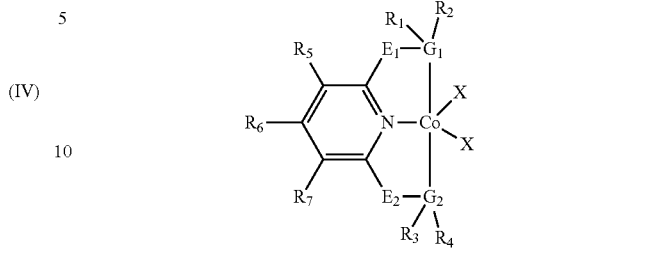

wherein $R_1$-$R_4$ are independently selected from the group consisting of hydrogen and alkyl, and wherein $R_5$-$R_7$ are independently selected from the group consisting of hydrogen, alkyl, and heteroalkyl; and
wherein $E_1$ and $E_2$ are independently selected from the group consisting of $CR_8$, and $C(R_8)_2$, wherein $R_8$ is selected from the group consisting of hydrogen, and alkyl; and
wherein $G_1$ and $G_2$ are independently selected from N and P; and
and
and wherein X is $R^{13}COO-$, where $R^{13}$ is alkyl and
wherein the cobalt complex of Formula (IV) is operable to participate in borylation of an arene or aromatic heterocycle.

7. The cobalt complex of claim 6, wherein $R_1$-$R_4$ are independently alkyl.

8. The cobalt complex of claim 7 having the structure:

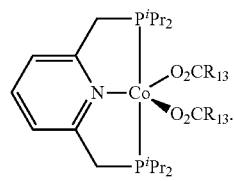

9. The cobalt complex of claim 7, having the structure:

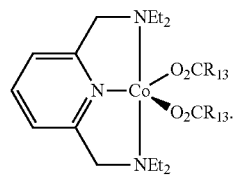

* * * * *